(12) United States Patent
Brockman et al.

(10) Patent No.: US 12,396,738 B2
(45) Date of Patent: Aug. 26, 2025

(54) DEVICE INCLUDING STEERING CABLES FOR CREATING A CAVITY OR A CHANNEL IN BONE

(71) Applicant: Stryker Corporation, Kalamazoo, MI (US)

(72) Inventors: Christopher Scott Brockman, Kalamazoo, MI (US); Geoffrey J. Vangemert, Portage, MI (US)

(73) Assignee: Stryker Corporation, Portage, MI (US)

( * ) Notice: Subject to any disclaimer, the term of this patent is extended or adjusted under 35 U.S.C. 154(b) by 756 days.

(21) Appl. No.: 17/556,194

(22) Filed: Dec. 20, 2021

(65) Prior Publication Data

US 2022/0110639 A1 Apr. 14, 2022

Related U.S. Application Data

(63) Continuation of application No. 16/545,685, filed on Aug. 20, 2019, now Pat. No. 11,259,818, which is a
(Continued)

(51) Int. Cl.
*A61B 17/16* (2006.01)
*A61B 17/00* (2006.01)
(Continued)

(52) U.S. Cl.
CPC ...... *A61B 17/1617* (2013.01); *A61B 17/1622* (2013.01); *A61B 17/1631* (2013.01);
(Continued)

(58) Field of Classification Search
CPC .... A61B 2034/715; A61B 2017/00327; A61B 17/1642; A61B 2017/00389;
(Continued)

(56) References Cited

U.S. PATENT DOCUMENTS 3,320,957 A 5/1967 Sokolik
4,294,233 A * 10/1981 Takahashi ............ A61B 1/0052
600/149
(Continued)

FOREIGN PATENT DOCUMENTS

DE 3840466 A1 6/1990
EP 3081252 A1 10/2016
(Continued)

OTHER PUBLICATIONS

International Search Report for Application No. PCT/US2020/028989 dated Nov. 6, 2020, 3 pages.
(Continued)

*Primary Examiner* — David W Bates
(74) *Attorney, Agent, or Firm* — Howard & Howard Attorneys PLLC

(57) ABSTRACT

A device for creating a cavity or a channel in bone. First and second steering cables are coupled to a flexible elbow or a tip of a shaft. A control assembly is operably coupled to the first and second steering cables and configured to tension one of the steering cables and slacken another one of the steering cables so as to flex the flexible elbow. The control assembly may include a steering block axially movable within a handle with a knob threadably coupled to the steering block. The steering block may be rotatably fixed within the handle. The first and second steering cables may be anchored to the steering block, such as to opposite sides of the steering block. The first steering cable may extend along a linear path, and the second steering cable may extend along a curved rib of the handle.

13 Claims, 15 Drawing Sheets

Related U.S. Application Data continuation of application No. 15/097,642, filed on Apr. 13, 2016, now Pat. No. 10,441,295, which is a continuation of application No. PCT/US2013/065002, filed on Oct. 15, 2013.

(51) Int. Cl.
    *A61B 17/3207*      (2006.01)
    *A61B 17/34*      (2006.01)
    *A61B 90/00*      (2016.01)

(52) U.S. Cl.
    CPC ...... *A61B 17/1642* (2013.01); *A61B 17/1671* (2013.01); *A61B 2017/00318* (2013.01); *A61B 2017/00389* (2013.01); *A61B 2017/00424* (2013.01); *A61B 2017/0046* (2013.01); *A61B 2017/00867* (2013.01); *A61B 17/162* (2013.01); *A61B 17/1626* (2013.01); *A61B 17/1697* (2013.01); *A61B 17/320708* (2013.01); *A61B 17/3472* (2013.01); *A61B 2090/062* (2016.02)

(58) Field of Classification Search
    CPC ... A61B 1/0052; A61B 1/0056; A61B 1/0057; B25J 9/065; A61M 25/0136; A61M 25/0147
See application file for complete search history.

(56) References Cited

U.S. PATENT DOCUMENTS

| | | | |
|---|---|---|---|
| 4,326,530 A | 4/1982 | Fleury, Jr. | |
| 4,607,626 A * | 8/1986 | Borodulin | A61H 21/00 604/105 |
| 4,874,371 A * | 10/1989 | Comben | A61B 1/0052 604/95.01 |
| 5,108,404 A | 4/1992 | Scholten et al. | |
| 5,209,749 A | 5/1993 | Buelna | |
| 5,224,488 A | 7/1993 | Neuffer | |
| 5,242,461 A | 9/1993 | Kortenbach et al. | |
| 5,282,821 A | 2/1994 | Donahue | |
| 5,292,330 A | 3/1994 | Shutt | |
| 5,295,980 A | 3/1994 | Ersek | |
| 5,306,272 A | 4/1994 | Cohen et al. | |
| 5,327,906 A * | 7/1994 | Fideler | A61M 25/0138 604/95.01 |
| 5,383,852 A * | 1/1995 | Stevens-Wright | A61M 25/0136 604/95.04 |
| 5,445,639 A | 8/1995 | Kuslich et al. | |
| 5,455,365 A | 10/1995 | Winter et al. | |
| 5,499,981 A | 3/1996 | Kordis | |
| 5,501,654 A | 3/1996 | Failla et al. | |
| 5,540,693 A | 7/1996 | Fisher | |
| 5,591,170 A | 1/1997 | Spievack et al. | |
| 5,624,431 A | 4/1997 | Gerry et al. | |
| 5,695,515 A | 12/1997 | Orejola | |
| 5,709,697 A | 1/1998 | Ratcliff et al. | |
| 5,814,044 A | 9/1998 | Hooven | |
| 5,843,103 A | 12/1998 | Wulfman | |
| 5,860,995 A * | 1/1999 | Berkelaar | A61B 17/29 606/174 |
| 5,885,299 A | 3/1999 | Winslow et al. | |
| 5,891,088 A * | 4/1999 | Thompson | A61M 25/0136 604/524 |
| 5,928,239 A | 7/1999 | Mirza | |
| 5,944,690 A * | 8/1999 | Falwell | A61M 25/0136 600/146 |
| 5,987,344 A | 11/1999 | West | |
| 6,027,462 A | 2/2000 | Greene et al. | |
| 6,036,682 A | 3/2000 | Lange et al. | |
| 6,036,698 A | 3/2000 | Fawzi et al. | |
| 6,059,739 A | 5/2000 | Baumann | |
| 6,224,604 B1 | 5/2001 | Suddaby | |
| 6,280,450 B1 | 8/2001 | McGuckin, Jr. | |
| 6,319,257 B1 | 11/2001 | Carignan et al. | |
| 6,331,166 B1 | 12/2001 | Burbank et al. | |
| 6,344,026 B1 | 2/2002 | Burbank et al. | |
| 6,358,251 B1 | 3/2002 | Mirza | |
| 6,383,188 B2 | 5/2002 | Kuslich et al. | |
| 6,423,081 B1 | 7/2002 | Lee et al. | |
| 6,425,887 B1 | 7/2002 | McGuckin et al. | |
| 6,440,062 B1 * | 8/2002 | Ouchi | A61B 1/00098 600/146 |
| 6,440,138 B1 | 8/2002 | Reiley et al. | |
| 6,454,727 B1 | 9/2002 | Burbank et al. | |
| 6,468,279 B1 | 10/2002 | Reo | |
| 6,468,289 B1 | 10/2002 | Bonutti | |
| 6,482,235 B1 | 11/2002 | Lambrecht et al. | |
| 6,491,681 B1 | 12/2002 | Kunis et al. | |
| 6,491,689 B1 | 12/2002 | Ellis et al. | |
| 6,540,693 B2 | 4/2003 | Burbank et al. | |
| 6,543,455 B2 | 4/2003 | Bonutti | |
| 6,547,432 B2 | 4/2003 | Coffeen et al. | |
| 6,558,390 B2 | 5/2003 | Cragg | |
| 6,575,978 B2 | 6/2003 | Peterson et al. | |
| 6,575,979 B1 | 6/2003 | Cragg | |
| 6,585,734 B2 | 7/2003 | Levinson | |
| 6,592,531 B2 | 7/2003 | Bonutti | |
| 6,592,559 B1 | 7/2003 | Pakter et al. | |
| 6,607,534 B2 | 8/2003 | Bonutti | |
| 6,626,903 B2 | 9/2003 | McGuckin, Jr. et al. | |
| 6,632,231 B2 | 10/2003 | Radisch, Jr. | |
| 6,647,281 B2 | 11/2003 | Morency | |
| 6,652,532 B2 | 11/2003 | Bonutti | |
| 6,652,548 B2 | 11/2003 | Evans et al. | |
| 6,659,105 B2 | 12/2003 | Burbank et al. | |
| 6,660,011 B2 | 12/2003 | Levinson | |
| 6,663,588 B2 * | 12/2003 | DuBois | A61M 25/0147 604/95.04 |
| 6,663,602 B2 | 12/2003 | Moeller | |
| 6,673,071 B2 | 1/2004 | VanDusseldorp et al. | |
| 6,676,658 B2 | 1/2004 | Burbank et al. | |
| 6,676,665 B2 | 1/2004 | Foley et al. | |
| 6,676,668 B2 | 1/2004 | Mercereau et al. | |
| 6,679,886 B2 | 1/2004 | Weikel et al. | |
| 6,689,145 B2 | 2/2004 | Lee et al. | |
| 6,699,206 B2 | 3/2004 | Burbank et al. | |
| 6,726,690 B2 | 4/2004 | Eckman | |
| 6,740,090 B1 | 5/2004 | Cragg et al. | |
| 6,746,451 B2 | 6/2004 | Middleton et al. | |
| 6,796,989 B2 | 9/2004 | Uflacker | |
| 6,805,675 B1 | 10/2004 | Gardeski et al. | |
| 6,814,734 B2 | 11/2004 | Chappuis et al. | |
| 6,821,276 B2 | 11/2004 | Lambrecht et al. | |
| 6,824,551 B2 | 11/2004 | Trerotola | |
| 6,833,000 B2 | 12/2004 | Levinson | |
| 6,835,198 B2 | 12/2004 | Bonutti | |
| 6,840,944 B2 | 1/2005 | Suddaby | |
| 6,849,084 B2 | 2/2005 | Rabkin et al. | |
| 6,863,672 B2 | 3/2005 | Reiley et al. | |
| 6,863,676 B2 | 3/2005 | Lee et al. | |
| 6,875,219 B2 | 4/2005 | Arramon et al. | |
| 6,899,716 B2 | 5/2005 | Cragg | |
| 6,913,594 B2 | 7/2005 | Coleman et al. | |
| 6,921,403 B2 | 7/2005 | Cragg et al. | |
| 6,923,813 B2 | 8/2005 | Phillips et al. | |
| 6,939,351 B2 | 9/2005 | Eckman | |
| 6,939,352 B2 | 9/2005 | Buzzard et al. | |
| 6,951,557 B2 | 10/2005 | Ellis et al. | |
| 6,960,172 B2 | 11/2005 | McGuckin, Jr. et al. | |
| 7,010,378 B2 | 3/2006 | Ohishi et al. | |
| 7,011,670 B2 | 3/2006 | Radisch, Jr. | |
| 7,014,633 B2 | 3/2006 | Cragg | |
| 7,074,236 B2 | 7/2006 | Rabkin et al. | |
| 7,087,058 B2 | 8/2006 | Cragg | |
| 7,108,704 B2 | 9/2006 | Trerotola | |
| 7,114,501 B2 | 10/2006 | Johnson et al. | |
| 7,131,981 B2 | 11/2006 | Appling et al. | |
| 7,134,437 B2 | 11/2006 | Bonutti | |
| 7,144,397 B2 | 12/2006 | Lambrecht et al. | |
| 7,153,315 B2 | 12/2006 | Miller | |

(56) References Cited

U.S. PATENT DOCUMENTS

| | | |
|---|---|---|
| 7,172,609 B2 | 2/2007 | Radisch, Jr. |
| 7,179,024 B2 | 2/2007 | Greenhalgh |
| 7,226,481 B2 | 6/2007 | Kuslich |
| 7,234,468 B2 | 6/2007 | Johnson et al. |
| 7,241,297 B2 | 7/2007 | Shaolian et al. |
| 7,282,055 B2 | 10/2007 | Tsuruta |
| 7,291,146 B2 | 11/2007 | Steinke et al. |
| 7,309,338 B2 | 12/2007 | Cragg |
| 7,329,267 B2 | 2/2008 | Weber |
| 7,331,958 B2 | 2/2008 | Falwell et al. |
| 7,341,594 B2 | 3/2008 | Shluzas et al. |
| 7,413,568 B2 | 8/2008 | Swanson et al. |
| 7,476,226 B2 | 1/2009 | Weikel et al. |
| 7,476,244 B2 | 1/2009 | Buzzard et al. |
| 7,500,977 B2 | 3/2009 | Assell et al. |
| 7,524,301 B2* | 4/2009 | Dubois .............. A61M 25/0136 604/95.04 |
| 7,604,611 B2 | 10/2009 | Falwell et al. |
| 7,615,044 B2 | 11/2009 | Scheibe et al. |
| 7,641,664 B2 | 1/2010 | Pagano |
| 7,658,537 B2 | 2/2010 | Coffeen et al. |
| 7,666,226 B2 | 2/2010 | Schaller |
| 7,666,227 B2 | 2/2010 | Schaller |
| 7,670,374 B2 | 3/2010 | Schaller |
| 7,670,375 B2 | 3/2010 | Schaller |
| 7,682,358 B2 | 3/2010 | Gullickson et al. |
| 7,682,378 B2 | 3/2010 | Truckai et al. |
| 7,686,809 B2 | 3/2010 | Triplett et al. |
| 7,699,849 B2 | 4/2010 | Eckman |
| 7,713,273 B2 | 5/2010 | Krueger et al. |
| 7,722,612 B2 | 5/2010 | Sala et al. |
| 7,749,225 B2 | 7/2010 | Chappuis et al. |
| 7,749,228 B2 | 7/2010 | Lieberman |
| 7,758,625 B2 | 7/2010 | Wu et al. |
| 7,815,650 B2 | 10/2010 | Shluzas et al. |
| 7,828,804 B2 | 11/2010 | Li et al. |
| 7,837,724 B2 | 11/2010 | Keeble et al. |
| 7,842,041 B2 | 11/2010 | Liu et al. |
| 7,846,206 B2 | 12/2010 | Oglaza et al. |
| 7,879,038 B2 | 2/2011 | Reiley et al. |
| 7,896,880 B2 | 3/2011 | Bonutti |
| 7,909,827 B2 | 3/2011 | Reiley et al. |
| 7,935,082 B2 | 5/2011 | Datta et al. |
| 7,935,141 B2 | 5/2011 | Randall et al. |
| 7,959,642 B2 | 6/2011 | Nobis et al. |
| 7,967,789 B2 | 6/2011 | Solar et al. |
| 7,967,829 B2 | 6/2011 | Gunderson et al. |
| 7,993,301 B2 | 8/2011 | Boyd et al. |
| 7,993,384 B2 | 8/2011 | Wu et al. |
| RE42,757 E | 9/2011 | Kuslich et al. |
| 8,021,365 B2 | 9/2011 | Phan |
| 8,021,366 B2 | 9/2011 | Phan |
| 8,034,088 B2 | 10/2011 | Pagano |
| 8,052,613 B2 | 11/2011 | Assell et al. |
| 8,083,687 B2 | 12/2011 | Parihar |
| 8,090,428 B2 | 1/2012 | de Villiers et al. |
| 8,128,633 B2 | 3/2012 | Linderman et al. |
| 8,142,367 B2 | 3/2012 | Gardeski et al. |
| 8,142,441 B2 | 3/2012 | Refai et al. |
| 8,216,296 B2 | 7/2012 | Wu et al. |
| 8,317,791 B2 | 11/2012 | Phan |
| 8,353,911 B2 | 1/2013 | Goldin et al. |
| 8,690,884 B2 | 4/2014 | Linderman et al. |
| 8,795,306 B2 | 8/2014 | Smith et al. |
| 8,827,981 B2 | 9/2014 | Liu et al. |
| 8,894,658 B2 | 11/2014 | Linderman et al. |
| 8,986,386 B2 | 3/2015 | Oglaza et al. |
| 9,119,639 B2* | 9/2015 | Kuntz .............. A61B 17/1642 |
| 9,247,929 B2 | 2/2016 | Melsheimer |
| 9,308,001 B2 | 4/2016 | Rodriguez |
| 9,308,013 B2 | 4/2016 | Casey et al. |
| 9,389,443 B2 | 7/2016 | Takakura et al. |
| 9,504,479 B2 | 11/2016 | Nino et al. |
| 9,730,707 B2 | 8/2017 | Sasaki |
| 9,839,443 B2 | 12/2017 | Brockman et al. |
| 10,441,295 B2 | 10/2019 | Brockman et al. |
| 10,806,896 B2* | 10/2020 | Davies .............. A61M 25/0136 |
| 11,191,575 B2 | 12/2021 | Kidman et al. |
| 2002/0016624 A1 | 2/2002 | Patterson et al. |
| 2002/0022856 A1 | 2/2002 | Johnson et al. |
| 2002/0029055 A1 | 3/2002 | Bonutti |
| 2002/0065485 A1* | 5/2002 | DuBois .............. A61M 25/0136 604/95.04 |
| 2002/0068974 A1 | 6/2002 | Kuslich et al. |
| 2003/0191474 A1 | 10/2003 | Cragg et al. |
| 2003/0220648 A1 | 11/2003 | Osorio et al. |
| 2004/0162559 A1 | 8/2004 | Arramon et al. |
| 2004/0267269 A1 | 12/2004 | Middleton et al. |
| 2005/0043737 A1 | 2/2005 | Reiley et al. |
| 2005/0060030 A1 | 3/2005 | Lashinski et al. |
| 2005/0075540 A1 | 4/2005 | Shluzas et al. |
| 2005/0113836 A1 | 5/2005 | Lozier et al. |
| 2005/0119662 A1 | 6/2005 | Reiley et al. |
| 2005/0182412 A1 | 8/2005 | Johnson et al. |
| 2005/0197661 A1 | 9/2005 | Carrison et al. |
| 2005/0203527 A1 | 9/2005 | Carrison et al. |
| 2005/0216018 A1 | 9/2005 | Sennet |
| 2005/0240193 A1 | 10/2005 | Layne et al. |
| 2005/0261692 A1 | 11/2005 | Carrison et al. |
| 2006/0030847 A1 | 2/2006 | McGuckin et al. |
| 2006/0085005 A1 | 4/2006 | Kenealy et al. |
| 2006/0100640 A1* | 5/2006 | Bolduc .............. A61B 17/00234 606/108 |
| 2006/0116689 A1 | 6/2006 | Albans et al. |
| 2006/0149268 A1 | 7/2006 | Truckai et al. |
| 2006/0184192 A1 | 8/2006 | Markworth et al. |
| 2006/0195106 A1 | 8/2006 | Jones et al. |
| 2006/0195107 A1 | 8/2006 | Jones et al. |
| 2006/0235338 A1 | 10/2006 | Pacheco |
| 2006/0271061 A1 | 11/2006 | Beyar et al. |
| 2007/0006692 A1 | 1/2007 | Phan |
| 2007/0021835 A1 | 1/2007 | Edidin |
| 2007/0055259 A1 | 3/2007 | Norton et al. |
| 2007/0055261 A1 | 3/2007 | Reiley et al. |
| 2007/0060933 A1 | 3/2007 | Sankaran et al. |
| 2007/0067034 A1 | 3/2007 | Chirico et al. |
| 2007/0068329 A1 | 3/2007 | Phan et al. |
| 2007/0123889 A1 | 5/2007 | Malandain et al. |
| 2007/0149990 A1 | 6/2007 | Palmer et al. |
| 2007/0198020 A1 | 8/2007 | Reiley et al. |
| 2007/0260270 A1 | 11/2007 | Assell et al. |
| 2007/0270863 A1 | 11/2007 | Melkent |
| 2007/0276392 A1 | 11/2007 | Beyar et al. |
| 2007/0282344 A1 | 12/2007 | Yedlicka et al. |
| 2007/0282345 A1 | 12/2007 | Yedlicka et al. |
| 2007/0293947 A1 | 12/2007 | Mansmann |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0058827 A1 | 3/2008 | Osorio et al. |
| 2008/0114364 A1 | 5/2008 | Goldin et al. |
| 2008/0208230 A1 | 8/2008 | Chin et al. |
| 2008/0294166 A1 | 11/2008 | Goldin et al. |
| 2008/0300574 A1 | 12/2008 | Belson et al. |
| 2009/0099641 A1 | 4/2009 | Wu et al. |
| 2009/0192357 A1* | 7/2009 | Torii .................. A61B 1/0052 600/149 |
| 2009/0198272 A1* | 8/2009 | Kerver .................. A61B 17/29 606/205 |
| 2009/0210046 A1 | 8/2009 | Shumer et al. |
| 2009/0270862 A1 | 10/2009 | Arcenio |
| 2009/0270892 A1 | 10/2009 | Arcenio et al. |
| 2009/0270893 A1 | 10/2009 | Arcenio |
| 2009/0287236 A1 | 11/2009 | Bakos et al. |
| 2009/0299282 A1 | 12/2009 | Lau et al. |
| 2010/0036381 A1 | 2/2010 | Vanleeuwen et al. |
| 2010/0082033 A1 | 4/2010 | Germain |
| 2010/0145431 A1 | 6/2010 | Wu et al. |
| 2010/0160921 A1 | 6/2010 | Sun et al. |
| 2010/0211076 A1 | 8/2010 | Germain et al. |
| 2010/0241123 A1 | 9/2010 | Middleton et al. |
| 2010/0280449 A1* | 11/2010 | Alvarez .................. A61B 34/71 606/1 |
| 2010/0298832 A1 | 11/2010 | Lau et al. |

(56) References Cited

U.S. PATENT DOCUMENTS

| | | |
|---|---|---|
| 2011/0024145 A1 | 2/2011 | Click et al. |
| 2011/0028980 A1 | 2/2011 | Click et al. |
| 2011/0098709 A1 | 4/2011 | Malandain et al. |
| 2011/0098759 A1 | 4/2011 | Trieu |
| 2011/0184447 A1 | 7/2011 | Leibowitz et al. |
| 2011/0251615 A1 | 10/2011 | Truckai et al. |
| 2011/0264074 A1* | 10/2011 | Tegg ............... A61B 5/062 604/523 |
| 2011/0295261 A1 | 12/2011 | Germain |
| 2011/0295262 A1 | 12/2011 | Germain et al. |
| 2012/0089125 A1* | 4/2012 | Scheibe ............ A61M 25/0147 604/523 |
| 2012/0130381 A1 | 5/2012 | Germain |
| 2012/0209273 A1 | 8/2012 | Zaretzka et al. |
| 2012/0239049 A1 | 9/2012 | Truckai et al. |
| 2012/0239072 A1 | 9/2012 | Rodriguez |
| 2012/0253226 A1 | 10/2012 | Parihar et al. |
| 2012/0277755 A1 | 11/2012 | Liu et al. |
| 2012/0330314 A1 | 12/2012 | Schaller et al. |
| 2013/0006232 A1 | 1/2013 | Pellegrino et al. |
| 2013/0012929 A1* | 1/2013 | Malkowski ............ A61B 17/29 606/1 |
| 2013/0012958 A1* | 1/2013 | Marczyk ............ A61B 17/2909 606/130 |
| 2013/0018473 A1 | 1/2013 | Cragg |
| 2013/0041403 A1 | 2/2013 | Cunningham et al. |
| 2013/0150831 A1 | 6/2013 | Griffiths |
| 2015/0011830 A1* | 1/2015 | Hunter ............... A61B 1/0016 600/118 |
| 2015/0112134 A1* | 4/2015 | Suehara ............... A61B 1/0052 600/109 |
| 2015/0141914 A1* | 5/2015 | Fasano ............... A61M 25/0113 604/95.01 |
| 2015/0305797 A1* | 10/2015 | Hassoun ............ A61B 17/2909 606/208 |
| 2015/0374889 A1* | 12/2015 | Lazarus ................ A61B 1/042 604/541 |
| 2015/0374890 A1* | 12/2015 | Lazarus ................ A61M 1/84 29/428 |
| 2016/0015250 A1* | 1/2016 | Suehara ............ A61M 25/0147 604/95.04 |
| 2016/0074028 A1* | 3/2016 | Castro ............... A61B 17/2909 606/130 |
| 2016/0192915 A1* | 7/2016 | Papenfuss .......... A61B 17/1633 606/130 |
| 2016/0228131 A1 | 8/2016 | Brockman et al. |
| 2017/0035576 A1 | 2/2017 | Schaller et al. |
| 2017/0245933 A1* | 8/2017 | Graham ................ A61B 17/29 |
| 2017/0325841 A1* | 11/2017 | Govari ................ A61B 1/0055 |
| 2018/0289436 A1* | 10/2018 | Jorgensen .......... A61B 18/1492 |
| 2018/0310982 A1* | 11/2018 | Worrell ............. A61B 18/1445 |
| 2019/0000405 A1 | 1/2019 | Shoup et al. |
| 2019/0038345 A1 | 2/2019 | Pellegrino et al. |
| 2019/0336730 A1* | 11/2019 | Cheng ............... A61M 25/0147 |
| 2019/0365388 A1 | 12/2019 | Brockman et al. |
| 2020/0170738 A1* | 6/2020 | Hasegawa ............. A61B 34/71 |
| 2021/0235969 A1* | 8/2021 | Solano Montenegro .................... A61B 1/018 |
| 2023/0149663 A1* | 5/2023 | Klein .................... A61B 34/71 604/95.04 |

FOREIGN PATENT DOCUMENTS

| | | |
|---|---|---|
| WO | 9951149 A1 | 10/1999 |
| WO | 2009155319 A1 | 12/2009 |
| WO | 2012125546 A1 | 9/2012 |
| WO | 2018218084 A2 | 11/2018 |
| WO | 2019200091 A1 | 10/2019 |

OTHER PUBLICATIONS

Partial International Search Report for Application No. PCT/US2020/028989 dated Sep. 16, 2020, 3 pages.
United States U.S. Appl. No. 17/603,148, filed on Oct. 12, 2021.
International Search Report for Application No. PCT/US2013/065002 dated Apr. 7, 2014, 5 pages.
English language abstract and machine-assisted English translation for DE 38 40 466 extracted from espacenet.com database on Jan. 8, 2018, 8 pages.

* cited by examiner

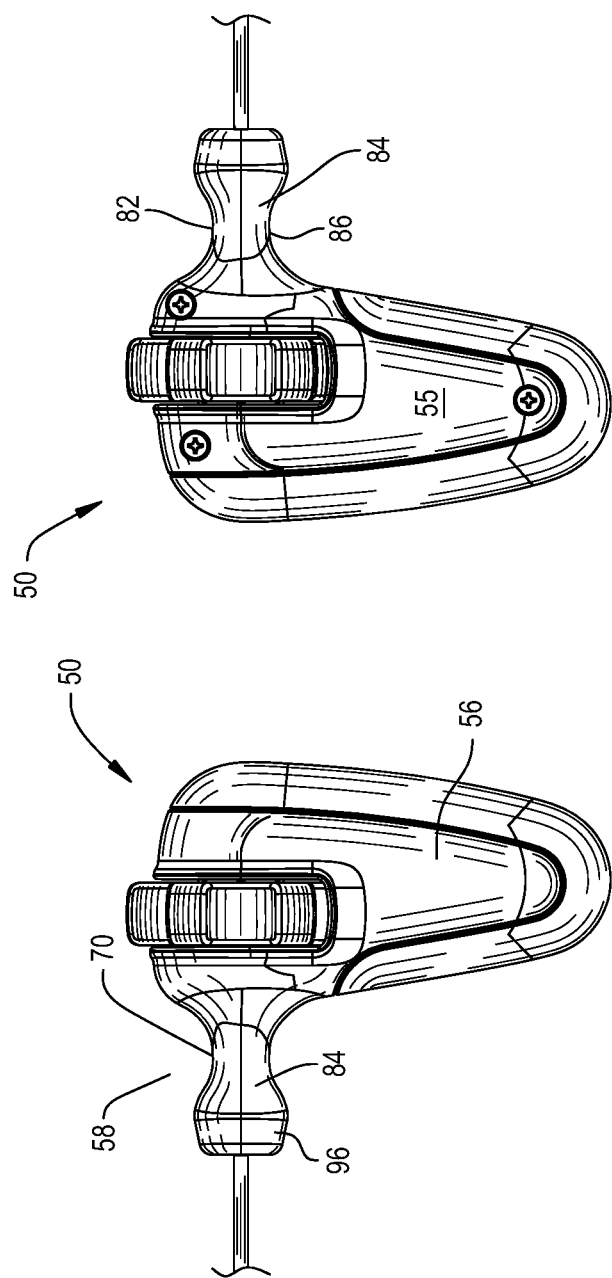

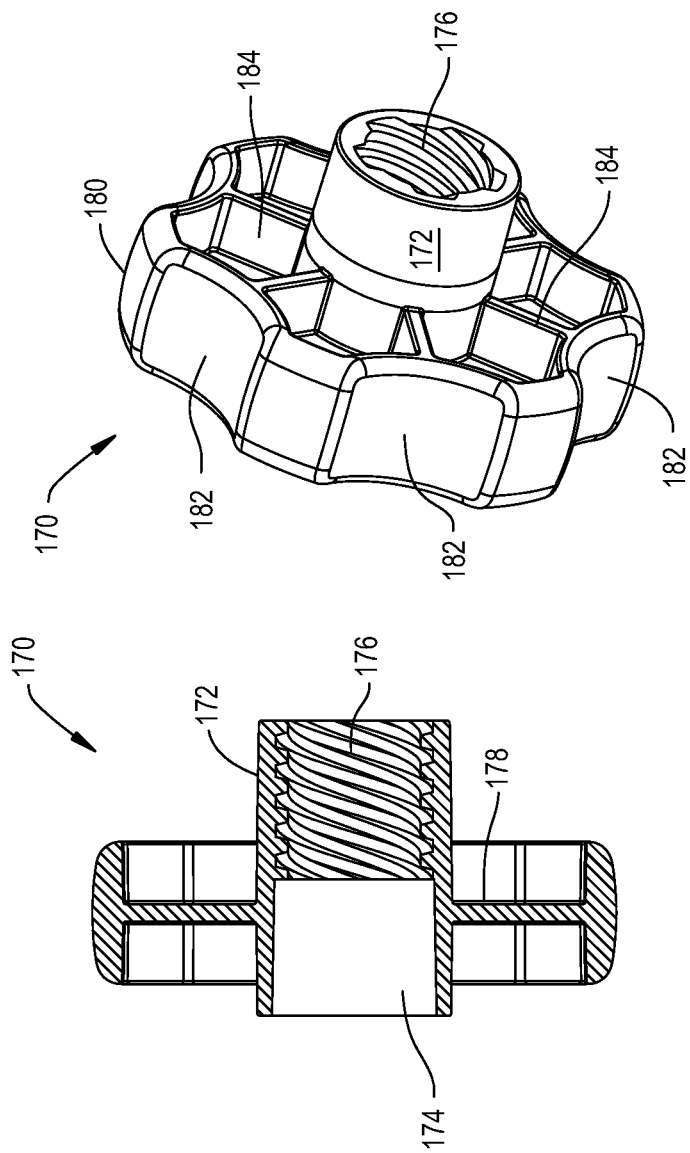

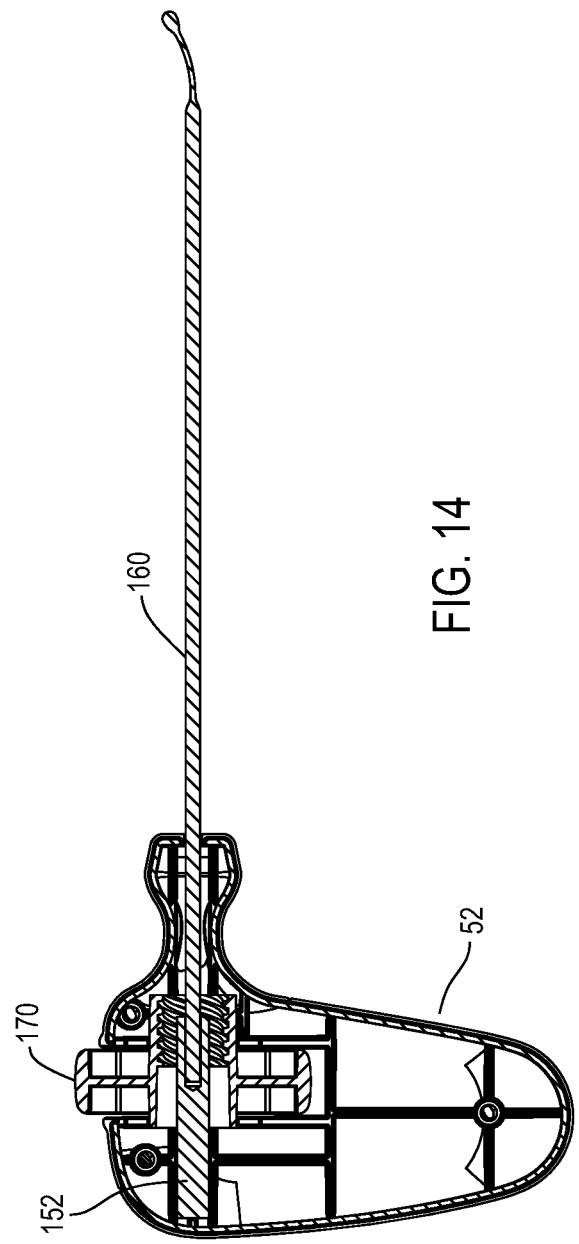

DEVICE INCLUDING STEERING CABLES FOR CREATING A CAVITY OR A CHANNEL IN BONE

CROSS REFERENCE TO RELATED APPLICATIONS

This is a continuation of copending U.S. application Ser. No. 16/545,685, filed Aug. 20, 2019, which is a continuation of U.S. application Ser. No. 15/097,642, filed Apr. 13, 2016, now U.S. Pat. No. 10,441,295, which is a continuation of International Application No. PCT/US2013/065002, filed Oct. 15, 2013, each of which is hereby incorporated by reference in its entirety.

FIELD OF THE DISCLOSURE

This disclosure relates generally to a device useful for creating a void space in living tissue such as bone. The device of this disclosure includes a handle with a control knob for regulating the setting of the device. The handle is constructed so that when the device is in different positions and positions and orientations relative to the practitioner using the device, the practitioner is able to easily hold the handle and set the knob.

BACKGROUND

There are a number of medical devices used to create void spaces such as cavities or channels in living tissue such as bone. One such device is a cavity creator. A cavity creator is a surgical tool assembly that, as implied by its name, forms a cavity in the tissue of a living being. A number of cavity creators are specifically designed to form cavities in hard tissue, more specifically, bone. This type of cavity creator may be used in a procedure generally known as a vertebral augmentation procedure. In a vertebral augmentation procedure, cement is injected into a vertebral body that is suffering from fracture so as to stabilize the vertebral body. It is believed that this stabilization reduces the pain the fracture would otherwise induce in the patient. As part of this procedure, to ensure a sufficient quantity of cement is introduced into the vertebra, it may be necessary to form a cavity, sometimes referred to as a void space, in the vertebra.

A cavity creator that forms a void space in a vertebra typically includes two components, an access cannula and a curette. The access cannula is a tube like device. The access cannula is inserted in the patient and into the vertebra to be filled with cement. The curette includes an elongated shaft dimensioned to extend through the lumen, the bore, of the access cannula. A tip is located at the distal end of the shaft. A handle is located at the proximal end of the shaft. Once the curette is seated in the access cannula the tip is positioned to extend radially, outwardly from the longitudinal axis of the access cannula. The rotation of the curette results in the pressing of the tip against the bone located outwardly from the access cannula. The pressing of the tip against the bone abrades the bone so as to form a cavity, the void space, internal to the vertebra that extends radially beyond the access cannula. Once this cavity is formed, the curette is withdrawn. Cement or other therapeutic agent is then introduced into the bone and more particularly the cavity that surrounds the open distal end of the access cannula.

Some curettes include a tip that is pivotally attached to the distal end of the curette rod. A drive shaft internal to the rod is selectively extended/retracted to pivot the tip between an orientation in which the tip is axially aligned with the shaft and orientation in which the tip is directed away from the shaft. Some of these curettes rely on a thumb wheel and gear assembly mounted to the curette handle to selectively extend/retract the drive shaft. Still other of these curettes include ratchet mechanisms again mounted to the handle, to extend/retract the drive shaft.

A disadvantage of a number of these curettes is that their internal components do not allow one to easily set the extended state position of their drive rods. This means that, in turn, it is difficult to set this type of curettes so as to with a degree of precision, control the extent to which the tip extends beyond the complementary access cannula. Further some of these curettes include numerous parts. As with any device, the more parts required to build the device increases the cost of providing the device.

Still another known curette includes a shaft with a tip that is formed integrally with and extends distally from the shaft. At least the connector that holds the tip to the shaft is formed from a superelastic shape memory material. This curette is initially seated in the access cannula so that connector and the tip are wholly disposed in the cannula. When the cavity creator is in this state, the connector is bent to generally conform to the shape of the access cannula. The shaft of the curette is extended to cause the tip and connector to extend forward from the access cannula. As the connector emerges from the constraining space of the access cannula, the potential energy of the connector is released. This causes the connector to return to its unconstrained, bent, state. By extension, this results in the movement of the tip radially away from the access cannula. Once the tip is in the desired position, the curette is rotated so as to press the tip against the adjacent bone.

The above-described curette includes a control knob for selectively extending/retracting the shaft. This knob, when rotated, moves towards and away from the curette. The practitioner then has to adjust his/her hand position relative to the handle in order to set the position of the tip. Having to take this extra step adds to the ergonomic complexity of using this type of curette.

Moreover, as a consequence of the rotation of the knob to extend the above-described curette, the overall proximal-to-distal length of this device increases. Often a fluoroscope is in close proximity to the cavity creator when this procedure is performed. The fluoroscope provides real time images of the bone in which the void space is being formed. The increasing length of the handle of this curette can make it difficult to position the curette around the fluoroscope.

Further, many curettes, regardless of the type of assemblies that pivot their tips, share a common problem. When the cavity creator with which one of these curettes is integral is in certain positions, it is difficult for the practitioner to hold the handle so as to rotate the handle and/or set the extent to which the curette shaft is extended. For example, there are times when the practitioner forms a void space that is centered on an axis that extends into the patient through a portal located on the side of the patient opposite the side of the patient against which the practitioner is standing. This is known as the contra-lateral side of the patient. Thus, if the practitioner is standing adjacent the left side of the patient, it may be desirable to create a cavity that is located in bone best accessed from the right side of the patient. The presence of equipment, for example a fluoroscope, may make it difficult for the practitioner to simply reposition himself/ herself adjacent the right side of the patient. In this situation, to form the cavity, the practitioner has to reach across the spine of the patient in order to insert the access cannula. When the curette is inserted into the access cannula, the handle does not simply face away from the practitioner as the handle would if located between the practitioner and the patient. Instead, the handle of the curette can be both spaced away from the practitioner and be directed towards the practitioner. To set the extended state position of the curette shaft or rod, the practitioner has to reach across the patient. This puts the hand of the practitioner in an awkward position relative to the component of the curette he/she needs to manipulate. This makes it difficult for the practitioner to set the curette to ensure that tip is properly positioned.

Furthermore, it should be understood that the creation of a void space involves more than simply extending and retracting the shaft integral with the curette. It is also necessary to rotate the curette to press the tip against the tissue to be removed. This means that the practitioner may be required to place his/her hands and fingers in an unusual position in order to both set the extension of the curette and rotate the curette.

Still another class of device used to form a void space in bone are channel creators. A channel creator is typically used to form an elongated bore, a channel, in the bone to which the channel creator is applied. These channels are typically smaller in cross sectional width and often longer in length than the cavities created by a cavity creator. The control members associated with a number of these devices have share a disadvantage with the cavity creators. It can be difficult to control the device depending on the orientation and position of the device relative to the practitioner.

SUMMARY

This disclosure relates to a new and useful medical/surgical device. The medical/surgical device of this disclosure includes a handle designed to be held by the practitioner in a single hand. An elongated member extends forward from the handle. A working tip is located at the distal end of the elongated member. Internal to the handle is a mechanism for regulating the actuation of the working tip. A knob is rotatably mounted to the handle so the practitioner can regulate the actuation of the working tip. The knob is rotatably mounted to the handle so that regardless of the orientation and position of the handle relative to the practitioner using the device, the practitioner can, with the thumb or fingers of the hand holding the handle set the knob.

In many versions of this disclosure the handle and knob are collectively dimensioned so that the knob is mounted to the handle so as to extend outwardly from opposed side surfaces of the handle and from a surface that bridges the side surfaces. This bridge surface may be the top surface, the front surface the bottom surface or the rear surface of the handle.

One version of this disclosure is a new and useful cavity creator for creating cavity in the tissue, such as bone, of a living being. The cavity creator of this disclosure includes an access cannula and a curette. The curette is constructed so that, through a wide range of orientations and positions of the cavity creator relative to the practitioner, the practitioner with minimal concentration and effort can manipulate the curette to set both the extent to which the tip extends from the access cannula and the orientation of the tip.

The curette of this disclosure includes a handle dimensioned and shaped to be held in between the thumb and fingers of a single hand. A shaft extends forward from the handle. At the distal end, the shaft includes an elbow formed from a superelastic shape memory material. A tip is located at the free end of the elbow. A drive head is affixed to the proximal end of the shaft. The drive head is disposed in the handle so as to be able to move from essentially the proximal end of the handle to essentially the distal end of the handle.

A knob is rotatably mounted to the handle. While the knob rotates, the longitudinal position of the knob relative to the handle is fixed. The handle and knob are collectively dimensioned so that the knob protrudes away from a top surface of the handle and adjacent sections of the opposed side surfaces. The knob is engaged with the drive head so that the rotation of the knob results in the extension or retraction of the drive head. The extension or retraction of the drive head results in the like movement of the curette shaft and attached components.

The above features of the curette of the void creator of this disclosure make it relatively easy to, with a single hand and throughout a wide range of curette orientations relative to the practitioner holding the curette, both rotate the handle and rotate the knob. This makes it relatively easy to, when the cavity creator is in different orientations, both set the extent to which the tip is extended from the access cannula and the orientation of the tip relative to an axis through the access cannula.

Another cavity creator of this disclosure includes an alternative curette. This curette includes an elbow that, while flexible, is not bent to a specific curvature. Steering cables extend proximally from the handle through the shaft and elbow to the tip. A mechanism internal to the handle selectively tensions and slacks the steering cables. The knob is the component the practitioner actuates so as to control the tensioning and slacking of the steering cables. The selective tensioning and slacking of the steering cables it is understood regulates the extent to which the elbow flexes the tip away the from the longitudinal axis of the shaft.

Another version of this disclosure is a channel creator. A prebent flexible elbow extends forward from the handle of this versions of the disclosure. A tip extends forward from the distal end of the elbow. The tip is formed from material that, when pushed forward, creates a channel in the tissue. A cable extends proximally from the tip, through the elbow and shaft into the handle. The knob is part of a drive assembly capable of selectively extending and retracting the cable. When the cable is in the retracted state, the cable places a tension on the elbow. The tension holds the elbow so that the elbow and tip are substantially in line with the longitudinal axis of the shaft. When the cable is in the extended state, the tension on the cable is reduced. Owing to the shape memory characteristics of the elbow, this allows the elbow to return the curved shape. When the elbow is so curved, the longitudinal axis of the tip is angled relative to the longitudinal axis of the shaft.

The handle, knob and control mechanism assembly of this disclosure may have other applications than setting the angular position of a void creating tip relative to the longitudinal axis of the shaft.

BRIEF DESCRIPTION OF THE DRAWINGS

The disclosure is pointed out with particularity in the claims. The above and further features and advantages of this disclosure are understood from the following Detailed Description taken in conjunction with the accompanying drawings in which:

FIG. 3 is a view of the left side of the handle of the curette;

FIG. 4 is a view of the right side of the curette;

FIG. 12 is a cross sectional view of the knob of the curette;

FIG. 13 is a perspective view of the knob;

FIG. 14 is a cross sectional view of the interior of the handle and the components internal to the handle of the curette;

DETAILED DESCRIPTION

I. Cavity Creator with First Curette

Figure 1:
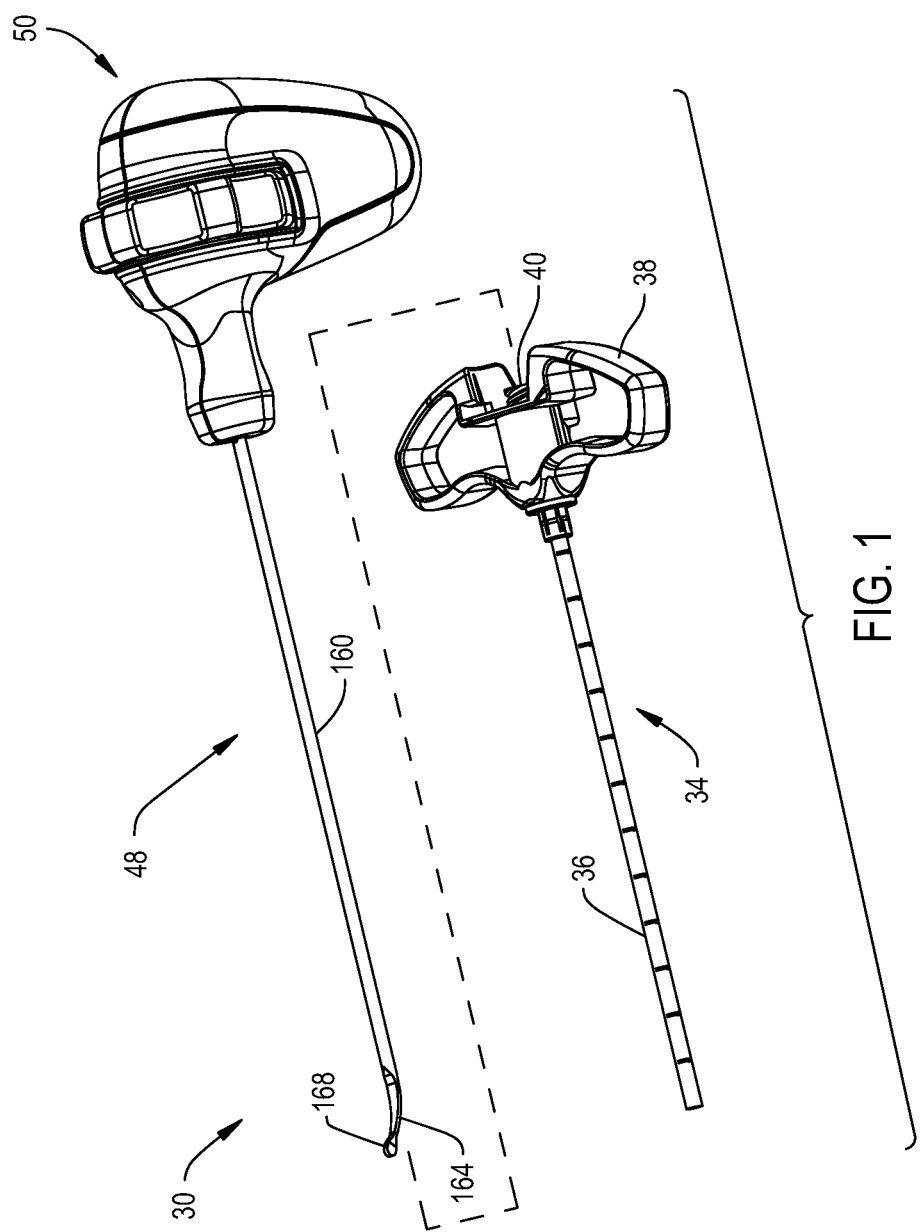
FIG. 1 is an exploded view of the components forming a cavity creator of this disclosure.

FIG. 1 depicts the components forming a cavity creator 30 of this disclosure. Specifically, cavity creator 30 includes an access cannula 34 and a curette 48. The access cannula 34 includes a tube 36 formed from material able to penetrate both soft tissue and hard tissue (bone). The distal end of tube 36 may have beveled edge to facilitate the insertion of the tube into the patient. (Here, "distal" is understood to mean away from the practitioner holding the cavity creator 30, towards the site to which the cavity creator is applied. "Proximal" is understood to mean towards the practitioner and away from the site to which the cavity creator 30 is applied.) A handle 38 is molded or otherwise secured over the proximal end of tube 36. The handle 38 is formed with a fitting 40 that opens into the lumen internal to tube 36. While not identified, the fitting is formed with threading. The threading facilitates the releasably coupling of either a cannula filled with cement or a syringe like device filled with cement to the access cannula.

Curette 48 includes a handle 50. A shaft 160 is moveably attached to the handle so as to be extended, move distally, and retracted, move proximally. At the distal end of the shaft 160 an elbow 164 is present. Elbow 164 is able to flex and return to its original bent shape. A tip 168 is located at the end of the elbow distal to the shaft. Shaft 160, including elbow 164 and tip 168, are moveably seated in the lumen of access cannula tube 36. By adjusting the extension/retraction of the curette shaft 160 the extent to which the tip 164 extends radially outwardly access cannula tube 36 is selectively set.

Figure 2:
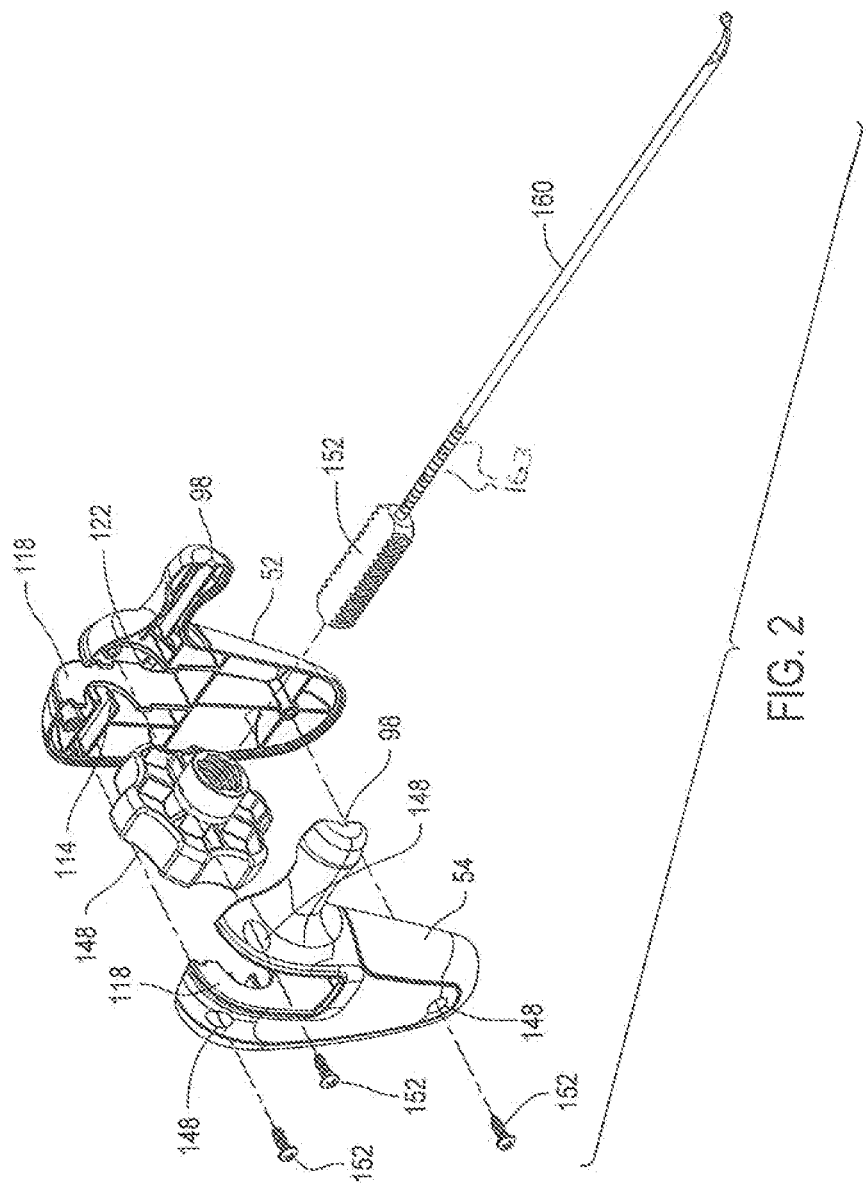
FIG. 2 is an exploded view of the components forming the curette of the cavity creator of this disclosure.
Figure 6:
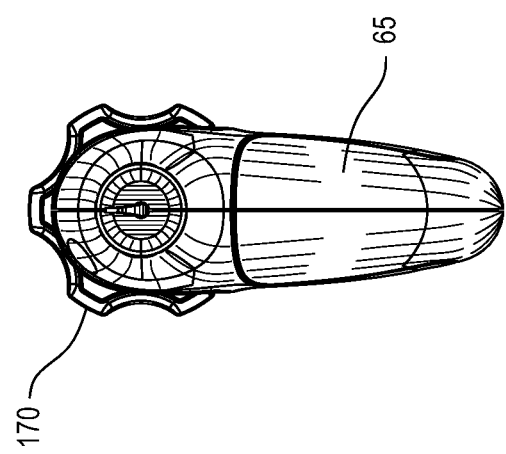
FIG. 6 is a plan view of the distally directed surface, the front of the handle.
Figure 5:
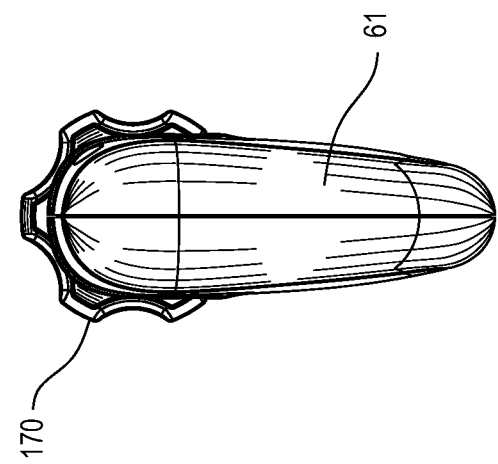
FIG. 5 is a plan view of the proximally directed surface, the back, of the handle.
Figure 10:
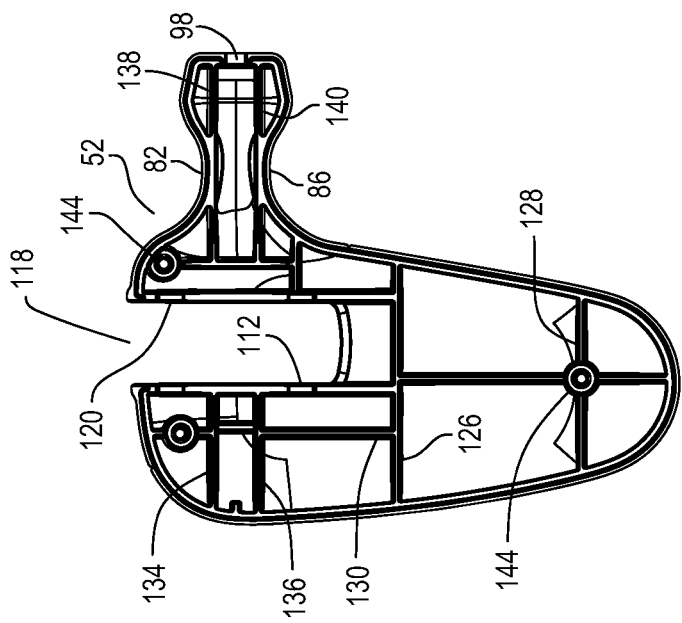
FIG. 10 is a plan view of the interior of one of the left side shell of the handle of the curette.
Figure 7:
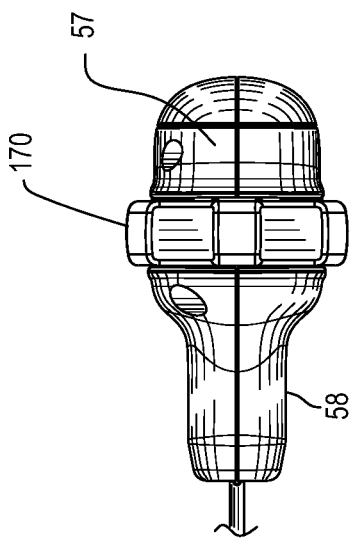
FIG. 7 is a plan view of the top of the handle of the handle.
Figure 8:
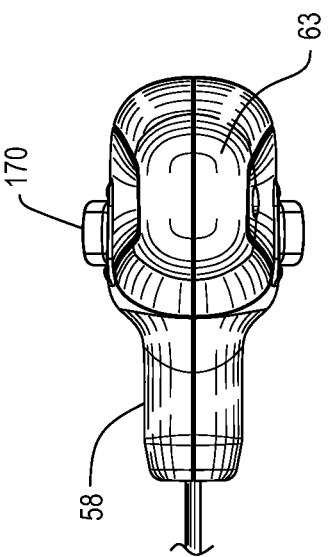
FIG. 8 is a plan view of the bottom of the handle and knob.
Figure 9:
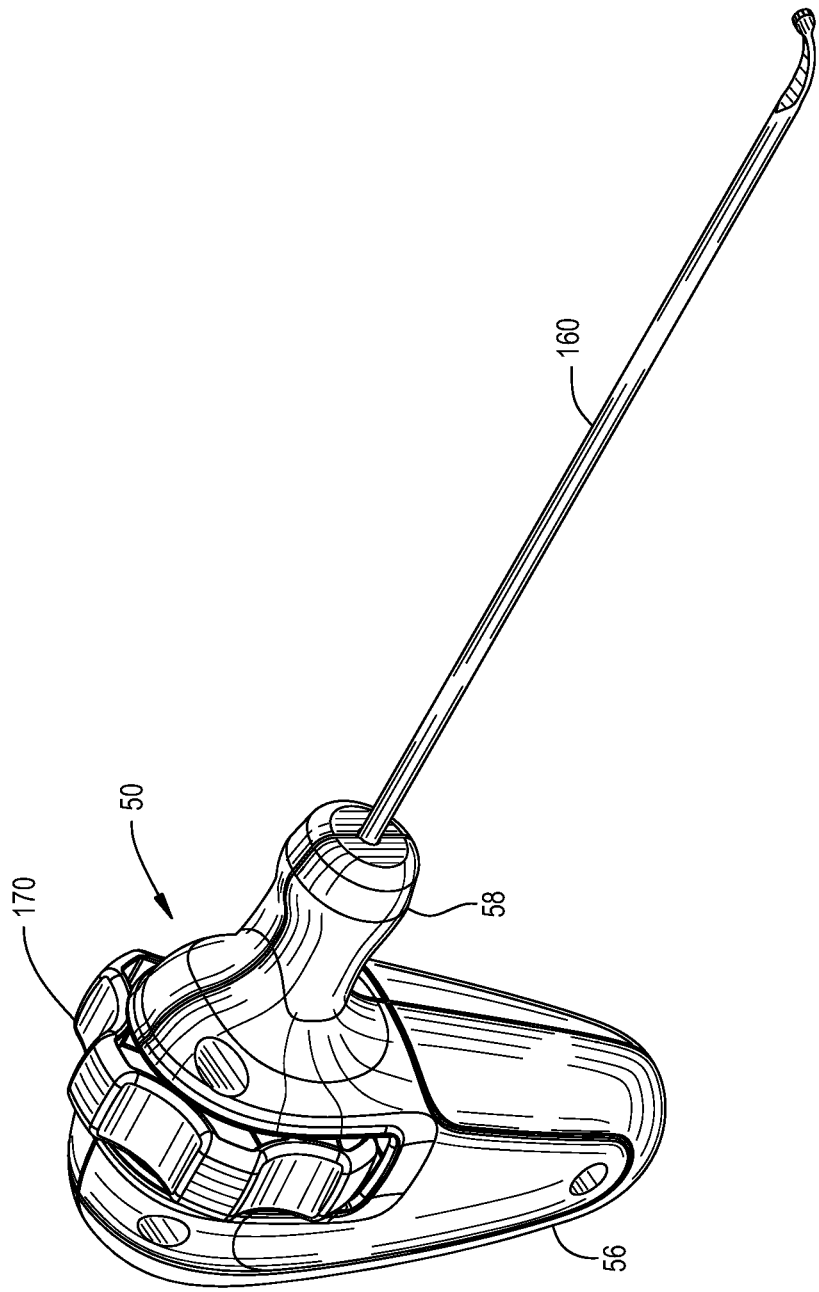
FIG. 9 is a perspective view of the handle and knob of the curette.

The curette handle 50, as seen in FIG. 2, includes a left shell 52 and a right shell 54. Shells 52 and 54, when assembled together form the body of handle 50. More particularly, the shells, as seen in FIGS. 3-10, form a base 56 and a stem 58 that projects distally forward from the base. Generally, the shells 52 and 54 are formed so that handle base 56 can be held between the thumb and fingers of a single hand. In some versions of the disclosure handle 50 is formed so that top to bottom, the base has a maximum length of between 6 and 13 cm. The top surface 57, the proximal facing surface 61, the bottom directed surface 63 and distal facing surface 65 of the base 56 are rounded. Base 56 has its widest width in the plane where the distance across the base immediately below the top surface 57 is at its widest. This width is between 1.5 and 5 cm. Below this plane, the side surfaces 55 of the base 56 taper inwardly toward each other. The proximal to distal length of the base is greatest in the plane from which the opposed ends of the arch that forms the curved top surface extends. This length is between 2.5 and 6 cm. Further it should be understood that top surface 57, proximal facing surface 61, bottom directed surface 63 and distal facing surface 65 of the handle should generally be considered bridge surfaces in that each of these surfaces, extends between, bridges, the opposed side surfaces 55.

Stem 58 extends forward from the base 56 around an axis that is located in or near the plane from which the opposed ends of the top surface curve upwardly and inwardly towards each other. The stem has neck 70. The neck has essentially parallel top and bottom surface 82 and 86. Curved side surfaces 84 extend between the opposed ends of the top and bottom surfaces. Top and bottom surfaces are spaced apart a distance that allows adjacent fingers to be placed across the surfaces 82 and 86 with no discomfort. Thus, surfaces 82 and 86 are at a maximum, spaced no more than 1.5 cm apart from each other.

Forward of neck 70 stem 58 is formed to have a head 96. Head 96 is generally circular in shape. Handle 50 is formed so that the head 96 extends radially outwardly beyond the surfaces 82, 84 and 86 of stem 58. Shells 52 and 54 are further formed to define in front, distal panel of the head a semi-circular cut out 98 (identified in FIG. 2). When the handle is assembled cutouts 98 go into registration so as to define a distal end opening in the front of stem head 96, opening not identified.

Each shell 52 and 54 is formed with a notch 118. Notches 118 extend downwardly from the top surfaces of shells 52 and 54. In the depicted version of the disclosure the proximal end of each notch 118 is defined by a web 112 internal to the shell that extends longitudinally top to bottom through the shell. The web 112 of left side shell 52 seen in FIG. 10. Each web 112 is further formed to have semi-circular cutout 114, one identified in FIG. 2, that opens into the notch. The distal end of each notch 118 is defined by a web 120 that, like web 120 extends inwardly from the outer portion of the shell 52 or 54 with which the web is integral. Web 120 is parallel to and spaced distally forward of web 112. Each web 120 is formed with a semicircular cutout 122, one identified in FIG. 2. Cutouts 114 and 122 are understood to be centered on the axis around which handle stem 58 is centered.

Internal to the shells 52 and 54 are additional webs that extend inwardly from the inner surfaces of the side panels of the shells. Two webs, webs 126 and 128, extend laterally, proximally to distally through the shell 52 or 54 with which the web is integral. The topmost of these webs, web 126 is the structural component of the shell against which webs 102 and 120 terminate. A web 130 that is parallel with and proximally spaced away from web 112 also extends upwardly from web 126.

Each shell 52 and 54 has two additional pairs of proximally-to-distally extending parallel webs. A first pair of webs, webs 134 and 136 extends forward from the inner surface of the rim of the shell that forms the proximal end of the shell. Webs 134 and 136 abut web 102. Web 134 is located above web 136. Webs 134 and 136 are equidistantly spaced from the axial line around which stem 58 is centered. A second pair of webs, webs 138 and 140, extends forward from the distal face of web 120. Webs 138 and 140 extend from the base 56 of the body of the handle and into stem head 96. Web 138 is coplanar with web 134. Web 140 is coplanar with web 136. Within the stem neck 70 each web 138 and 140 has a break, not identified. Thus while not identified it should be understood that each web 138 has a proximal section located primarily in base 50 of the body and a distal section located in the stem head 96.

The left side shell, shell 52 is formed to have three posts 144 that extend inwardly from the inner face of the side panel of the shell. Each post 144 is formed with a closed end bore (not identified). Right side shell 54 is formed to have three openings 148, identified in FIG. 2. Each opening 148 is formed in a recess 146 located inwardly from the side panel of the shell 54. When shells 52 and 54 are assembled together to form the body of handle 50, each right side shell opening 148 is in registration with one of the posts 144 formed in the left shell 52. Fasteners 152 that extend through the right shell openings 148 into the left shell posts 144 hold the shells together to form the body of the handle 50.

Figure 11:
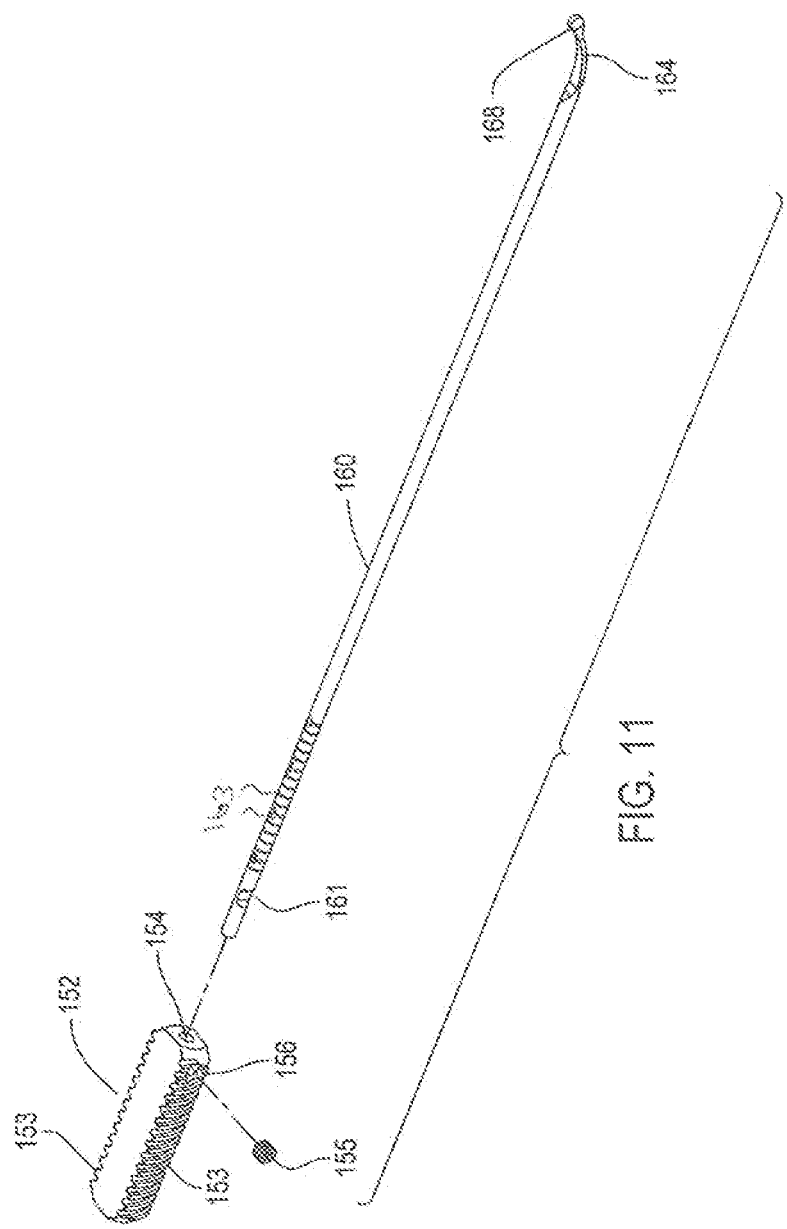
FIG. 11 is an exploded view of the curette shaft and the components connected to the shaft.

Curette shaft 160, now described with reference to FIG. 11, is generally tubular in shape. Shaft 160 is formed of material that, when the shaft is axially loaded resists axial buckling of the shaft. The shaft 160 is also formed from a biocompatible metal. Shaft 160 has a diameter that allows the shaft to slide in and out of the opening in the housing stem defined by cutouts 98.

A drive head 152 is located at the proximal end of shaft 160. In cross section, in planes perpendicular to the longitudinal axis of shaft 160, the drive head can be considered to be oval in shape. Drive head 152 is dimensioned to move within the space between webs 134 and 136, through openings defined by cutouts 114 and 122 and in the space between webs 138 and 140. The longitudinally extending opposed curved side surfaces of the drive head 152 are formed with threading 153.

The proximal end of curette shaft 160 is disposed in a bore 154 that opens in the distally directed face of the drive head 152 and extends proximally from that face. A set screw 155 holds shaft 160 to drive head 152. Set screw 155 is disposed in a threaded longitudinally extending bore 156 that extends from bore 154 to a side surface of the drive head. Screw 155 seats in an indentation 161 formed in shaft 160. Forward of drive head 152 indicia 163 (seen in FIGS. 2 and 11) are formed on shaft 160. The depicted indicia 163 are circular rings.

Elbow 164 is formed from a shape memory material, sometimes called a superelastic material. This is a material that, once subjected to a force will deform and, upon release of the force, will return to the original shape. One biocompatible superelastic material from which elbow 164 is formed is a nickel titanium alloy known as Nitinol. In some versions of the disclosure, shaft 160, elbow 164 and tip 168 are formed out of a single piece of Nitinol. The curette 48 is constructed so that elbow 164 extends outwardly from the plane that extends perpendicularly relative to the top-to-bottom longitudinal axis through handle 50. The elbow 164 subtends an arc that, extending distally forward from shaft 160, curves upwardly away from the shaft. In some versions of this disclosure, elbow 164 subtends an arc of between 20 and 50°.

Tip 168 is integral with or attached to the free end, the distal end, of elbow 164. In the illustrated version of the disclosure, tip 168 is oblate circle. Tip 168 has a diameter that is greater than the width of the elbow 164. Here elbow "width" is understood to be the distance across the minor axis of the elbow 164. Generally it should be understood that shaft 160, elbow 164 and tip are formed so as that the elbow can be flexed sufficiently such that the each of these components can fit in and slidably move in the lumen of the access cannula tube 36.

A knob 170, seen best in FIGS. 12 and 13, is rotatably attached to the curette handle 50 to control the extension/retraction of shaft 160 relative to the handle. The knob 170 is formed to have tubular shaped hub 172. Hub 172 defines a bore 174 of sufficient diameter that drive head can seat in and move within the hub. The hub 172 is further formed so that the distal section of the inner surface of the hub has threading 176 that extends into the bore 174. Hub threading 176 is designed to engage threading 153 integral with drive head 152. The outer diameter of hub 172 is such that the proximal end of the hub can seat in and rotate in the circular opening formed by shell cutouts 114 and the distal portion of the hub can seat in and rotate in the circular opening formed by shell cutouts 122. The overall length of hub 172 is such that when curette 48 is assembled, the proximal end of the hub is approximately flush with the proximal surfaces of webs 112 and the distal portion of the hub is located forward of webs 120.

A flange 178, generally in the shape of a washer extends radially outwardly from the outer surface of hub 172. A ring 180 extends circumferentially around the outer perimeter of flange 178. Ring 180 extends proximally and distally relative to the flange 178. The ring has a proximal to distal length that allows the ring to be seated in the single notch in the body of the curette handle 50 formed by notches 118. Ring 180 is formed with indentations 182 that function as finger grips. Webs 184 extend outwardly from the opposed surfaces of flange 178. Each web 184 extends between the outer surface of the hub 172 and the inner surface of the ring 180 to provide reinforcing strength to the knob 170.

The components forming curette 48 are dimensioned so that when curette 48 is assembled, knob ring 180 projects outwardly from the opposed side surfaces 55 and the handle body and the interconnecting top surface 57. More particularly, the ring indentations 182 are located outwardly from these body surfaces. In many versions of the disclosure, the portion of knob that protrudes radially outwardly out at least 1 mm from these surfaces of the body subtends an arc of at least 150°. In many versions of the disclosure the continuous exposed section of the knob extends through an arc of at least 180°. In more preferred versions of the disclosure the exposed portions of the knob subtend an arc of at least 200°. For ease of operation in many versions of the disclosure, curette 48 is designed so that the arcuate section of the knob that protrudes radially outwardly from the body of the handle at least 180° extends at least 2 mm outwardly from the adjacent top and side surfaces of the handle.

The initial step of using cavity creator 30 of this disclosure is the insertion of the access cannula 34 into the bone in which the void space, the cavity, is to be created. Curette 48 is then fitted to the access cannula 34. More particularly, the curette elbow 164 is bent so the shaft 160, elbow 164 and tip can be fitted into the lumen, the bore, of access cannula tube 34. When the cavity creator 30 is in this state, shaft 160 is in the fully retracted state so tip 168 is in closest position relative to the handle. When curette 48 is in this state, most of the body of the drive head 152 is disposed in the spaced internal to the handle 50 proximal to knob 170, between webs 134 and 136.

Figure 15:
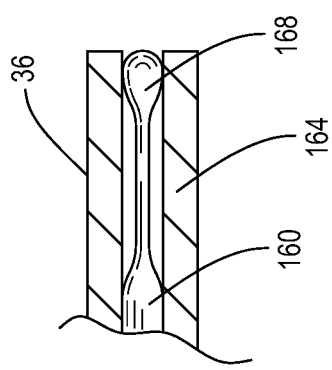
FIG. 15 is a cross sectional view of the distal end of the cavity creator when the tip of the curette is in the retracted state.

Owing to the dimensioning of the components forming cavity creator 30, when the cavity creator is in this state elbow 164 and tip 168 are, as seen in FIG. 15, disposed within the distal section of access cannula tube 36.

The cavity creator process continues with the extension of shaft 160. The practitioner extends the shaft by rotating knob 170. Given that the position of the knob on handle 50 is fixed, the rotation of the knob is transferred through knob threading 176 and drive head threading 153 to the drive head 152. The rotation of the knob against the drive head would be expected to cause the drive head 152 and, by extension, shaft 160 to move forward. However, the resistance of the bone adjacent the distal end of access cannula tube 36 prevents tip 168 from protruding outwardly. The ability of tip 168, elbow 164 and shaft 160 to resist axial loading means that, instead of the tip moving distally, the rotation of the knob 170 results in the handle moving proximally. More specifically, the handle 50 moves proximally away from access cannula fitting 40. More specifically the distally directed face of stem head 86 moves away from fitting 40. This movement results in one or more of shaft indicia being exposed adjacent the access cannula fitting 40. The number of exposed indicia provides the practitioner with an indication of the length of the exposed proximal section of shaft 160.

The practitioner then rotates the handle while simultaneously applying a distally directed force. These forces result in the tip 168 being pressed against the surrounding bone. This pressing of the tip against the bone abrades the bone so as to leave a void space that is located radially outwardly the distal open end of access cannula tube 36. The practitioner presses inwardly on the handle until the distally directed face of handle stem head 96 again presses against the access cannula fitting 40.

Thus at the end of the process a void, a cavity, is formed immediately forward the distal end of the access cannula tube 36. This void has a depth, axial distance from tube 36 to the distal end of the void, equal in distance to the distance to which the handle 50 originally was displaced proximally away from the cannula 34. This is why the practitioner monitors the exposure of the shaft indicia 163, to determine the extent to which the handle was originally displaced. As part of this procedure it should be further understood that the shaft may be rotated back and forth around an arc of less than 360°. This results in a like rotation of elbow 164 and tip 168. Consequently the void space formed by the cavity creator 30 of this disclosure will occupy an arc of less than 360° around the distal end of the access cannula tube 36. Thus, using the cavity creator 30 of this disclosure, it is possible to both control the depth of the void space that is created as well as the degree to which the void space circumferentially surrounds access cannula tube 36.

Figure 16:
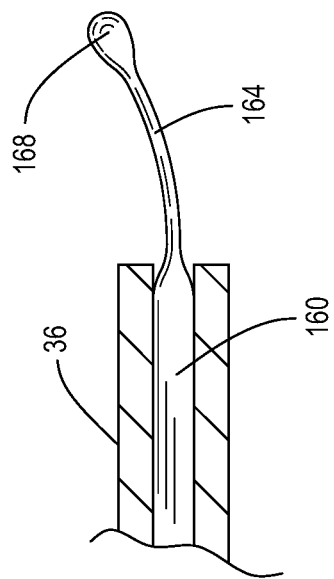
FIG. 16 is a side view when the tip of the curette is in the extended state.

In an alternative use of the cavity creator of this disclosure, the practitioner advances the shaft 160 while simultaneously holding curette stem 58 against the access cannula fitting 40. The forward movement of the shaft 160 results in the movement of elbow 164 out of the distal end of the access cannula tube 36. The freeing of the elbow 164 from the constraint of the tube releases the potential energy of the elbow; the elbow flexes towards the formed curved shape of the elbow. This flexing results in the movement of tip 168 radially away from the longitudinal axis of the access cannula as seen in FIG. 16.

At this time the tip 168 presses against the surrounding bone. Handle 50 is rotates so as to cause a like rotation of the tip 168. Tip 168 presses against the bone. This pressing of the tip against the bone abrades the bone so as to leave a void space that is located radially outwardly the distal open end of access cannula tube 36.

Once the void space is created, the practitioner rotates the thumb so as to retract tip 168 back into the access cannula tube 34. Curette 48 is then withdrawn from the access cannula 32. The practitioner is then able to perform the next part of the procedure for which the creation of the void space was required.

Curette handle 50 of the cavity creator 30 of this disclosure can be held in a single hand. In some procedures the cavity creator 30 is oriented so the distally directed face of handle stem 58 generally faces away from the practitioner. When curette 48 has this orientation relative to the practitioner, it is a simple task to, with fingers, hold the base 56. When the handle 50 is so grasped, the stem neck easily sits between the forefinger and the middle finger. The practitioner uses the thumb of the hand holding the handle to rotate knob 170.

In some procedures, cavity creator 30 is oriented so that the distally directed face of handle stem 58 is generally directed towards the practitioner. When the handle is so oriented, the practitioner can easily hold the handle from the top such that the fingers are disposed against one of the side surfaces 55 and the thumb against the opposed side surface 55. Knob 170 is rotated by the repositioning of the thumb from against the side surface 55 to against the knob. Thus, regardless of the orientation of the cavity creator 30, the practitioner is able to, with minimal effort, grasp the curette handle 50 and rotate the knob 170 so as to both extend/retract the tip and rotate the tip.

It should further be understood that when knob 170 is mounted to the handle 48 to rotate in a plane that is fixed relative to the handle. This means that as the knob rotates the practitioner does not have to reset the thumb or finger used to rotate the knob in order to compensate for the shifting position of the knob relative to the handle.

In many versions of this disclosure, the drive head and knob threading 153 and 176 are formed so that a complete 360° rotation of the knob results in the linear displacement of the shaft by a maximum of 1.2 cm. This allows the practitioner to, by only slightly rotating the knob 170, finely control the extent to which the tip 168 extends radially from the access cannula tube 36. A related feature is that with a single movement, typically of the thumb the practitioner can rotate knob 170 at least 180°. This is because the knob protrudes from both the top surface 57 and side surfaces 55 of the handle. This means with a single movement of the thumb the practitioner can advance shaft 160 a distance of at least 0.6 cm. Collectively these design features mean that the cavity creator of this disclosure provides the practitioner with the ability to advance the tip by both relatively fine distances or, when required, by a relatively long distance in the short time required to engage in full stroke of the thumb or finger.

Curette 48 of this disclosure essentially only has two moving parts; the shaft and attached components; and knob 170. Thus given that this curette has relatively few components, in comparison to curettes with more moving components, it can be more economical to provide.

II. Alternative Curette for Cavity Creator

Figures 17, 18:
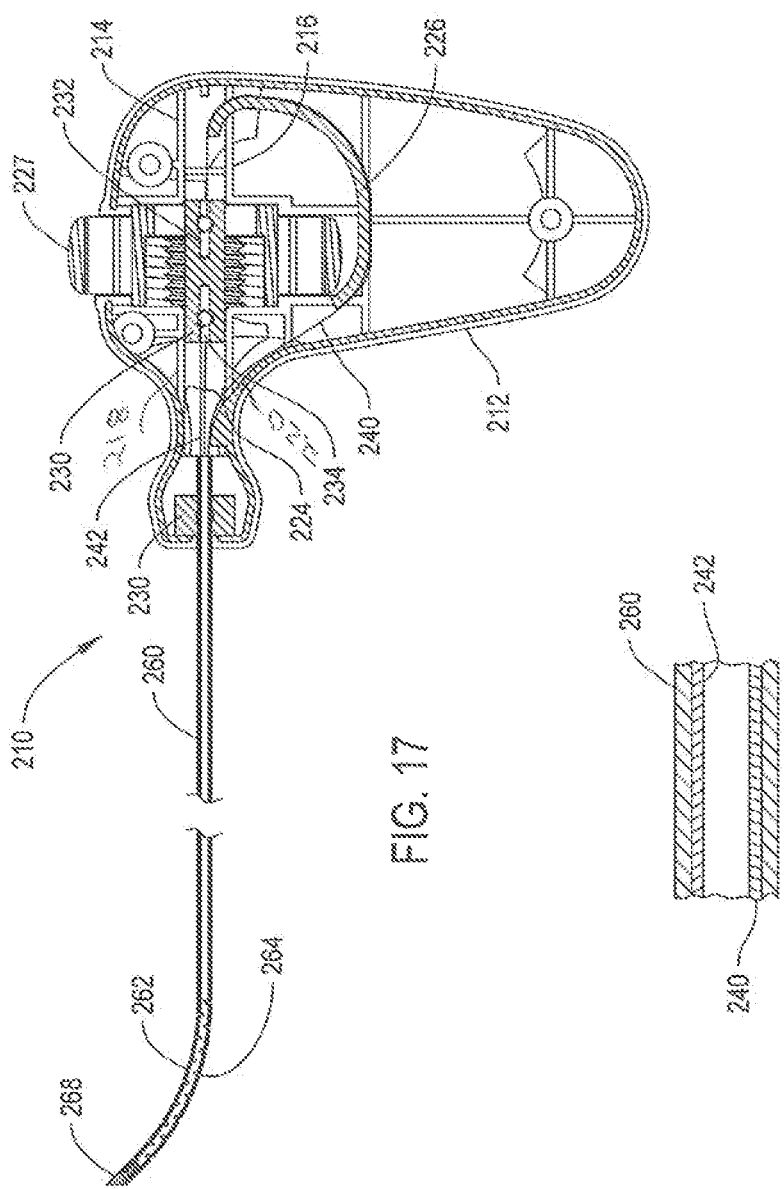
FIG. 17 is a cross sectional view of an alternative curette of this disclosure.
FIG. 18 is a enlarged cross sectional view of the shaft of the curette of FIG. 17.

FIG. 17 depicts in cross section an alternative curette 210 that includes the features of this disclosure. Curette 210 is used with access cannula 34 (FIG. 1) to form an alternative cavity creator.

Curette 210 includes a handle 212. Handle 212 has the general outer shape and dimensions of handle 50 of curette 48. Internal to the handle 212 are webs 214 and 216 that are analogues to webs 134 and 136, respectively. Also internal to the handle are webs 218 and 220. Webs 218 and 220 are analogues to webs 138 and 140, respectively. Webs 218 and 220 do not extend completely into the stem of handle 212. Internal to the handle a rib 224 extends inwardly from the bottom of the neck of the stem. Extending distally, the overall height of the rib decreases as the rib 224 curves downwardly. Handle 212 is also formed to have a curved rib 226. Rib 226 is generally C-shaped. On end of rib 226 is located above and adjacent the distal end of web 216. Rib 226 then curves downwardly and distally forward. From the lowest position with the handle rib 226 curves upwardly so as to approximately point to rib 224.

Figure 21:
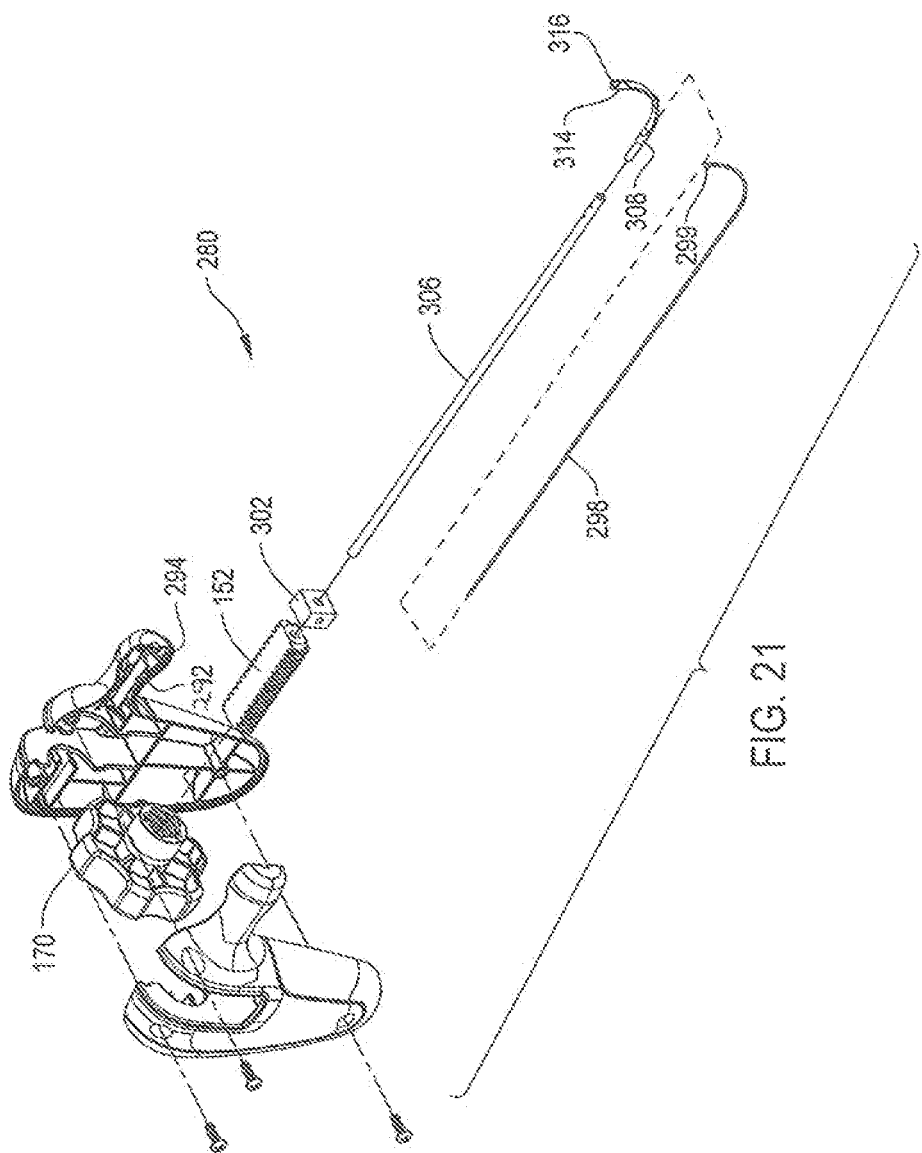
FIG. 21 is a exploded view of the creator of FIG. 19.

A shaft 260 extends forward the distally directed face of the stem of handle 212. A hollow shaft 260 is formed from stainless or Nitinol and is tubular in shape. The proximal end of shaft 260 is seated in a block 230 of handle 212. Block 230 is similar to below described block 302 of FIG. 21. Internal to handle 212 are webs with cutouts similar to cutouts 294 also seen in FIG. 21. Owing to the seating of the block 230 in the cutouts, block 230 is inhibited from rotating within the stem of handle 212. Shaft 260 is statically mounted to the block 230. Thus shaft 260, like block 230, is static relative to handle 212.

A flexible elbow 262 extends forward from the proximal end of shaft 260. In some versions of the disclosure, shaft 260 and elbow 262 are formed as a single component. Slots 264, one identified, are cut into the elbow to provide the elbow with flexibility. A tip 268 extends forward from the distal end of elbow 262. Tip 268 is formed from material and is shaped so that when the tip is rotated and pressed against bone, the tip abrades the bone. Shaft 260, elbow 262 and tip 268 are understood to be dimensioned so that these components can slidably fit within the axially extending lumen of access cannula tube 36. A number of cavity creators of this version are constructed so that when shaft 260 is fully seated in the access cannula tube 36, handle 212 abuts the access cannula fitting 40, and the elbow 262 is flexed straight, tip 268 projects at least 1.5 cm forward of the tube 36. In more preferred versions of the disclosure when the cavity creator of this disclosure is in this state, the tip 268 extends at least 2.5 cm forward from the access cannula tube 36.

Two steering cables 240 and 242 extend forward from handle 212 through shaft 260 and elbow 262. As seen best in FIG. 18, cables 240 and 242 are located on opposed sides of the shaft 260 and, while not seen, opposed sides of the elbow. Also, while not seen the shaft 260 may be formed with opposed lumens wherein each cable extends through a separate one of the lumens. These lumens may be formed in ribs that project inwardly into the center bore of the shaft. Further, the shaft may be solid so that the lumens in which the cables 240 and 242 are disposed are two parallel bores that extend axially through the shaft. The distal ends of steering cables 240 and 242 are attached to opposed sides of the proximal portion of tip 268. Alternatively, the opposed distal ends of the steering cables 240 and 242 attached to opposed sides of the distal end of elbow 262.

The proximal ends of the steering cables 240 and 242 are attached to a steering block 230 disposed in handle 212. Steering block 230 has the same generally oval cross sectional shape of drive head 152. The sides of the steering block 230 are formed with threading (not illustrated) similar to the threading 153 integral with drive head 152 (FIG. 11). Steering block 230 is formed with a closed end bore 232 that extends distally forward from the proximally directed face of the block. A closed end bore 234 extends proximally rearward from the distally directed face of the block 230. Bores 232 and 234 are coaxial.

The proximal end of steering cable 240 is anchored in steering block bore 232. Cable 240 extends proximally from the steering block over the surface of rib 226 that faces proximally and downwardly. From rib 226 cable 240 extends over rib 224 and into shaft 260. The proximal end of cable 242 is anchored in steering block bore 234. Cable 242 extends approximately along a linear path distally forward from the steering block 230 into and through shaft 260.

Curette 210 includes a knob 227 similar to knob 170 (FIGS. 12 and 13). A difference between the two knobs is that the hub 228 of knob 227 is slightly shorter than the hub 172 of knob 170. Knob 227 is rotatably mounted to handle 212 in the same general manner in which knob 170 is mounted to handle 50. The threading internal to knob hub 228 engages the complementary threading on the outer side surfaces of steering block 230.

A cavity creator that includes curette 210 is readied for use in the same general manner in which cavity creator 30 is readied for use. Prior to inserting shaft 260, elbow 262 and tip 268 in the access cannula 34, knob 227 is rotated to place the steering block 230 in the neutral position. The neutral position is the position in which owing to the position of the block, steering cables 240 and 242 impose essentially identical forces on the distal end of the elbow 262 or the tip 268. When these forces are essentially identical, the elbow 262 and tip 268 are held so as to be essentially longitudinally aligned with the longitudinal axis of shaft 260. When the curette is in this state, the shaft 260, the elbow 262 and tip 268 can be inserted into the access cannula tube 36.

To create a cavity using this cavity creator, the cannula is pushed distally forward so as to cause tip 268 to project forward of the access cannula tube 36. As part of this process knob may be rotated to set the orientation of the elbow 262 and tip 268 relative to the shaft 260. For example if there is a desire to direct the tip upwardly as seen in FIG. 17, knob is rotated to move steering block 230 proximally. This movement, in turn, causes the steering block 230 to pull steering cable 242 proximally while simultaneously reducing the tension the block places on steering cable 240. This specific tensioning/slacking of the steering cables results in cable 242 pulling on the component to which the distal end of the cable 242 is attached so that the elbow 262 flexes as seen in FIG. 17.

Alternatively, curette 210 can be set so that elbow 262 and tip 268 are directed downwardly, opposite the orientation seen in FIG. 17. This setting is achieved by rotating the knob 227 so that steering block 230 is displaced distally forward. This displacement of the steering block causes the block to simultaneously urge steering cable 240 proximally while reducing the tension that is placed on cable 242. This results in forces being placed on the component to which the distal ends of the cables are applied that flex the cable downwardly such that the tip 268 points towards a location opposite the location to which the tip is directed in FIG. 17.

Once the tip 268 is oriented in the desired direction, the practitioner may oscillate the tip by rotating the handle 210 through an arc of less than 360°. This results in the formation of a void space forward of the distal end of the access cannula tube 36 that does not extend completely around the tube. The rotational position of this void space is understood to be set based on the setting of the angular position of curette tip 268.

Curette 210 of this version of the disclosure provides the practitioner with the means to set the angular orientation of the tip 268 relative to shaft 262. This provides a further means to allow the practitioner to selectively form a void space in the bone regardless of the orientation in which the handle is being held. Thus, if the practitioner finds it necessary to hold the handle 212 upside down, wherein the top surface is directed towards the patient, by setting the angular orientation of the tip the practitioner can form a void space that is located upwardly relative to the portal in the bone through which the cavity creator is inserted in the patient.

Still a further feature of this version of the disclosure is that by selectively adjusting both the extent to which tip 268 is angularly offset from shaft 260 and the extent to which the tip is advanced forward from access cannula tube 36, the practitioner can form a void that while extending a 1 cm or more form the tube 36 does not project appreciably radially outwardly from the tube.

III. Channel Creator

Figure 19:
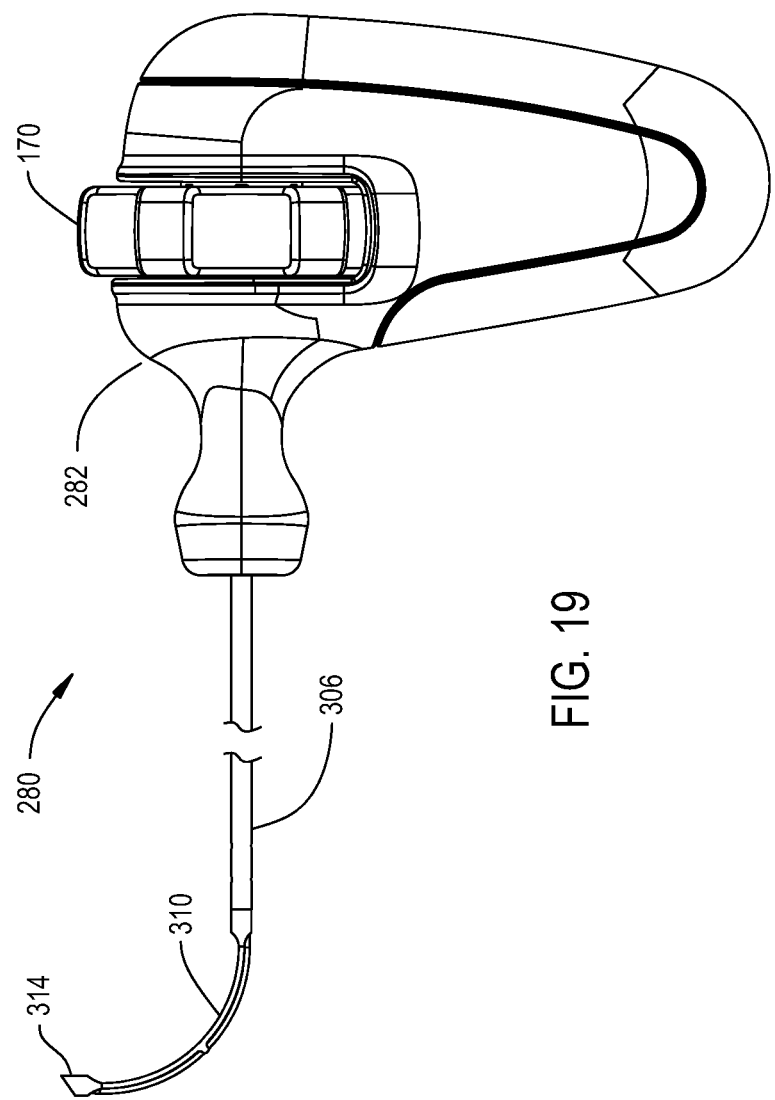
FIG. 19 is a side plan view of a channel creator of this disclosure.
Figure 20:
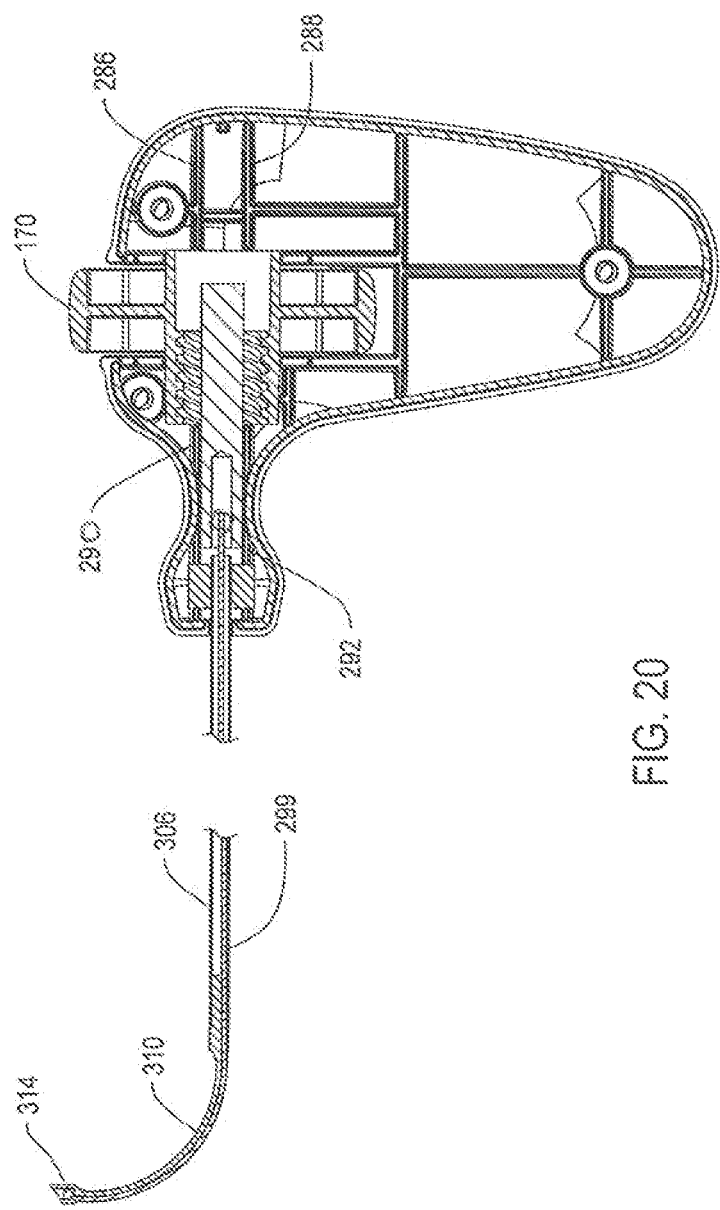
FIG. 20 is a cross-sectional view of the channel creator of FIG. 19.

A channel creator 280 incorporating the features of this disclosure is now described with reference to FIGS. 19 and 20. Channel creator 280 includes a handle 282 from which a shaft 306 extends distally forward. A pre-bent elbow 310 formed from flexible shape memory material extends forward from the distal end of shaft 306. A tip 314 extends from the distal end of elbow 310.

Handle 282 has the same general shape as previously described handles 50 and 212. Internal to handle 282 are webs 286, 288, 290 and 292. Webs 286 and 288 are substantially identical to previously described webs 134 and 136, respectively. Webs 290 and 292 are similar to previously described webs 138 and 140, respectively. Webs 290 and 292 are shaped to define rectangular cutouts 294 in the sections of the webs disposed within the head of the handle stem.

Previously described knob 170 is rotatably mounted to handle 282. A block 302 is seated in handle stem. More particularly block 302 is seated in cutouts 294. Webs 290 and 292 and block 302 are collectively dimensioned so they abut. Webs 290 and 292 thus hold the block 302 static in handle 282.

Shaft 306 extends distally forward from the stem of handle 282. Shaft 306 is formed from stainless steel or Nitinol and is tubular so as to have an axially extending lumen, (lumen not identified). The proximal end of shaft 306 is statically mounted in block 302. Not identified is the bore in the block 302 through which shaft 306 extends. A bent elbow 310 is mounted to and extends distally forward from the distal end of shaft 306. Elbow 310 is formed from a flexible shape memory material such as a nickel titanium alloy. In some versions of the disclosure, elbow 310, when not flexed, subtends an arc of between 45 and 90°.

In the depicted version of the disclosure, elbow 310 is formed so as to have a cylindrical stem 308. While not identified it can be seen from FIG. 20 that the stem has a elongated groove that extends along the portion of the elbow that becomes the outer curved surface of the elbow.

A tip 314 extends forward from distal end of elbow 310. Tip 314 is formed from material such as Nitinol. In this version of the disclosure, the tip is shaped so that when the tip is pressed forward, the tip will penetrate, form a bore or channel in bone or other tissue. In the depicted version of the disclosure, tip 314 is formed integrally with the elbow 310. The tip is formed to define a bore 316 that extends proximally from the distal end of the tip. Bore 316 is a closed end bore. While not seen in the drawings, the tip 314 is formed with a longitudinally extending notch. The notch is contiguous with and extends proximally from the proximal end of bore 316.

A number of channel creators of this version are constructed so that when shaft 306 is fully seated in the access cannula tube 36, handle 282 abuts the access cannula fitting 40 and elbow 310 is flexed straight, tip 314 projects at least 2 cm forward of the tube 36. In more preferred versions of the channel creator of this disclosure when the channel creator is in this state, the tip 314 extends at least 3 cm forward from the access cannula tube 36.

Drive head 152 is slidably disposed in handle 282. More particularly, the drive head is slidably disposed between webs 286 and 290 located above the block and webs 288 and 292 located below the block. Knob 170 engages and moves the drive head 152 proximally and distally within the handle 282 as previously described.

A tensioning cable 298 is attached to and extends distally forward of the drive head 152. Cable 298 extends through the lumen of shaft 306. By extension, the cable 298 extends through block 302. The cable extends forward of the shaft and through the groove formed in elbow stem 308. Cable 298 then extends around the outer curved surface of elbow 310. At the distal end, the cable has a spherical head 299. Cable head 299 is seated in the bore 316 formed in tip 314. The portion of the elongated body of the cable 298 immediately proximal to the head 299 is disposed in the section of the notch formed in the tip 314 that extends proximally away from the bore 316. Cable 298 and tip 314 are collectively formed so that cable head 299 cannot be pulled through the notch.

Channel creator 280 is used in combination with access cannula 34 to form a channel in the bone to which the channel creator is applied. A channel differs from a void space formed by a curette in that a channel tends to be narrower in cross section and longer in length. The access cannula 34 is initially inserted into the bone in which the channel is to be formed. Knob 170 is then rotated so as to induce the proximal movement of the drive head 152 and, by extension, cable 298. The rearward movement of the cable causes the cable to straighten out elbow 310. The elbow 310 can be straightened, flexed, so that tip 314 is becomes substantially aligned with the longitudinal axis of shaft 306. Once the elbow is so straightened. Shaft 306, elbow and tip can be slip fitted in the lumen of access cannula tube 36.

Tip 314 is shaped so that by reciprocating the channel creator 280 back and forth the tip forms a channel in the bone to which the tip is applied. The extent to which the path of the channel extends radially away from the distal end of the access cannula tube 36 is a function of the flexure of the elbow 310. The flexure of the elbow is set by rotating knob 170. More specifically, the knob 170 can be rotated to advance the drive head 152 and by extension, cable 298, forward. This results in the lessening of the extent to which the cable 298 places a straightening tension on the elbow. The lessening of this tension cause the release of the potential energy of the material forming the elbow. This energy returns the elbow to the flexed, bent, shape. By controlling the extent which the elbow is allowed to return to the flexed shape, the practitioner regulates the extent to which the channel creator 280, when advanced, forms a channel that extends radially from the access cannula tube 36.

Typically, the components forming cavity creator 280 are selected so that when elbow 310 is fully flexed, fully bent, the distal end of the tip 314 is radially spaced a minimum 1.5 cm from the longitudinal axis of shaft 306. In many versions of the disclosure, the cavity creator 280 is constructed so that when the elbow 310 is so flexed, the distal end of the tip 314 is radially spaced at least 2.5 cm from the longitudinal axis of shaft 306.

The rotational position of the channel relative to the access cannula tube 36 is set by rotating the handle 282. Thus, prior to rotating the knob 170 to set the curvature of the elbow 310 the practitioner may rotate the handle 282. This rotation establishes the rotation direction in which the tip 316 is directed as the elbow returns to the curved state. The illustrated version is designed so that the practitioner knows that the elbow when fully flexed bends away from the bottom surface of the handle 282.

IV. Alternative Embodiments

The foregoing is directed to specific versions of this disclosure. For example, an alternative curette of this disclosure may not have the single component shaft-elbow-tip of the disclosed disclosure. In an alternative version of the disclosure, the tip may be pivotally attached to the shaft. In these versions of the disclosure, a drive rod with drive head is connected to the handle. The handle having the knob of this disclosure extends/retracts the drive rod so as to pivot the tip relative to the handle.

In the described version of the disclosure, the knob is disposed in and rotates along an axis that is coaxial with shaft 160. This is not meant to be limiting. In an alternative version of the disclosure, the knob is mounted to the handle so as to rotate around an axis that is orthogonal or otherwise angled relative to the axis of the shaft. Still in some versions of the disclosure, the knob may not rotate about an axis that intersects or otherwise overlaps the longitudinal axis of the shaft.

Also there is no requirement that in all versions of the disclosure, the bridge surface from which the knob extends be the top surface. Thus in some versions of the handle bridge surface from which the knob extends may be one of the distally directed, bottom or proximally facing surfaces.

Likewise, when the knob is provided, there is no requirement that it include the described indentations. In an alternative version of the disclosure the outer circumferential surface of the knob that is gripped by the thumb or finger may be formed from a material that facilitates gripping. These materials include textured plastic or rubber.

In some versions of the disclosure, the rotating handle may be replaced by a lever or switch and a ratchet mechanism.

Curette 48 of this disclosure may also be used as a stand alone device. Alternatively, the curette may be incorporated into other assemblies.

While the foregoing description is directed specifically to the cavity creator of this disclosure, the features of this disclosure are not so limited. The handle 50 and knob 170 assembly of this disclosure may be incorporated into other medical devices where it is desirable to provide the practitioner with one-handed control of both the orientation of the device and setting of a moving component that extends from the handle. For example handle 50, drive head 152 and knob 170 may be used to selectively extend/retract the shaft of another medical device. These devices include elongated forceps or scissors used in arthroscopic or endoscopic procedures. The component or components that extend from and the handle and controlled by the knob may not even be rigid. For example, the one or more flexible steering cables may extend from the handle. These distal ends of these steering cables extend to a flexible device such a fluid delivery catheter or an electrode assembly that is inserted in the patient. The selective tensioning of these steering cables is controlled by the selective rotation of the knob 170. It should be appreciated that in these versions of the disclosure, the drive component/components that are connected to and actuated by the rotation of knob will be different from the disclosed drive head. For example, if the components controller by the knob are cables, the drive component/components may be one or more spools that are connected to the knob so as to rotate upon rotation of the knob.

Figure 22:
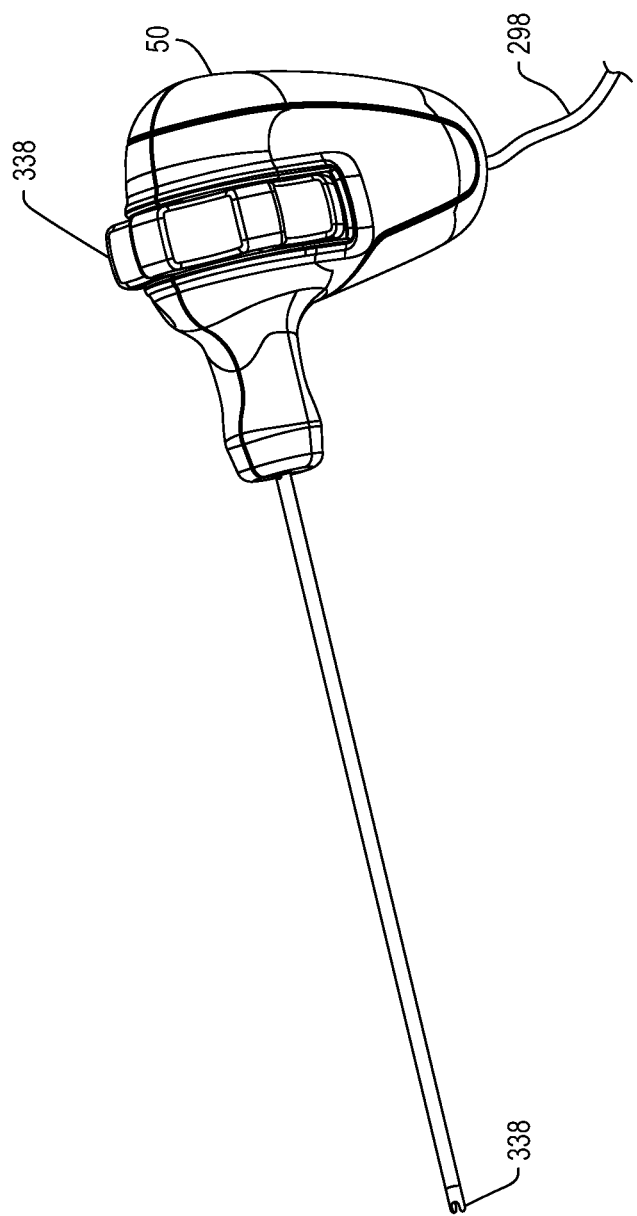
FIG. 22 is a perspective view of an electrosurgical tool constructed in accordance with this disclosure.

Likewise the component regulated by the knob may in some versions of the disclosure not be a component that performs a mechanical drive functions. The knob in some versions of this disclosure may be a component that controls the state of an electrical signal. Thus the knob function as the component that sets the position of the contact of a switch or the wiper of a potentiometer. Thus, as depicted in FIG. 22, one construction of this disclosure is one in which attached to the distal end of a shaft 336 is an electrode 338 (monopolar or bipolar). In these versions of the disclosure, the rotation of knob 332, by setting a switch and/or potentiometer internal to the handle sets the state of the control signal output from the handle 330 over a cable 298 back to a control console (not part of the present disclosure and not illustrated). Based on the state of the signal, the control console regulates the on/off state of the signal sourced to the electrode and/or the magnitude of the current or the level of the potential of the sourced current.

Further, this disclosure is not limited to constructions of the disclosure wherein there is only a single manually actuated control member attached to the handle. Thus in a version of the disclosure wherein the device includes a shaft with an electrode tip, the tip may be selectively positionable through the use of steering cables or a tension cable relative to the shaft. In these versions of the disclosure, the knob be used to set the angular position of the electrode relative to the shaft. A second control member may be used to regulate the application of a current to the electrode.

In some embodiments of these versions of the disclosure, the second control member may be a second knob. This second knob may or may not be parallel to the first knob. In still other embodiments of this disclosure, the second manually actuated control member may be another type of component such as a slide switch or a push button switch.

In the described versions of the disclosure, the shafts that extend distally from the handle are all shown as being straight. This should be interpreted as a limiting feature of this disclosure. In some versions of the disclosure, the shafts, while rigid, may be formed with one or more curved sections or is formed to have a shape that is continuously curved. Likewise, while the shafts of the described versions of the disclosure may be interpreted to be rigid, this characteristic should not be interpreted as a limiting feature of this disclosure. In some versions of the disclosure, the shafts may be understood to be formed out of material that can be bent. This would allow the practitioner to, at the start of the procedure place custom bends in the shaft to facilitate the shaping of the device for the specific patient and procedure. In these versions of the disclosures it would be understood that the driven components internal to the shaft would likewise be able to bend in order to properly function after this shaping.

In still other versions of this disclosure, the distal end of the prebent, flexible elbow may actually be the tip of the device. For example, in one version of this embodiment of the disclosure, the device functions as a cement delivery cannula. This type of cannula holds cement for discharge into bone such as a vertebral body. A cement delivery cannula of this disclosure includes a shaft and a prebent, flexible elbow which have contiguous longitudinally extending through bores. In these versions of the disclosure, the proximal end of the shaft extends to a fitting that projects proximally from the handle. The fitting is designed for connection to a unit capable of supplying bone cement to the cannula. For reasons apparent below, this fitting is designed to rotate around an axis that extends from the handle. One cement delivery device to which this cannula can be attached is disclosed in the Applicant's U.S. Pat. No. 7,658,537, issued 9 Feb. 2010, the contents of which are explicitly incorporated herein by reference. The shaft itself is connected to the handle knob similar to how shaft 160 is connected to knob 170. Thus the knob is rotated to selectively extend or retract the elbow relative to the handle. The distal end of the elbow is understood to be open.

The practitioner uses the cement delivery cannula of this disclosure by placing this cannula in an access cannula similar to access cannula 34. When the cement delivery cannula is placed in the access cannula the cement delivery cannula is initially set so the elbow is in the retracted state. The components of this system are designed so that when the elbow is so retracted, the elbow is fully disposed in the access cannula tube. This typically assumes the access cannula is already fitted in the patient. The unit capable of supplying cement is then connected by the handle fitting to the shaft of the cement delivery cannula. The knob is then rotated to set the extent to which the elbow extends forward from the distal end of the access cannula.

Once the position of the cement delivery cannula is so set, the cement delivery unit is actuated. This typically involves the proximal movement of a plunger. This results in the forcing of cement out of the cement delivery unit and through the shaft and elbow of the cement delivery cannula and out of this elbow.

Thus this version of this disclosure makes it possible for a practitioner to establish the location forward of the cement delivery cannula from which the cement will be discharged. This location setting in addition to being a radial distance is also a rotational setting. The practitioner establishes this setting by rotating the handle. This handle rotation it is understood results in a like rotation of shaft and elbow of the cement delivery cannula around the longitudinal axis of the access cannula.

Accordingly, it is an object of the appended claims to cover all such variations and modifications that come within the true spirit scope of this disclosure.

The invention claimed is:

1. A device for creating a cavity or a channel in bone, the device comprising:
    a handle;
    a shaft coupled to the handle and comprising a proximal portion seated within the handle, a tip located forward of the handle, and a flexible elbow between the proximal portion and the tip;
    a first steering cable coupled to the flexible elbow or the tip of the shaft;
    a second steering cable coupled to the flexible elbow or the tip of the shaft; and
    a control assembly comprising a knob that is rotatably coupled to the handle and operably coupled to the first steering cable and the second steering cable, wherein the knob is configured to be rotated to tension one of the first steering cable and the second steering cable and slacken the other one of the first steering cable and the second steering cable so as to flex the flexible elbow, wherein the control assembly comprises a steering block axially movable within the handle, wherein the knob is threadably coupled to the steering block, and wherein the first steering cable and the second steering cable are anchored to the steering block, and wherein the end of the first steering cable and the end of the second steering cable are coaxially arranged.

2. The device of claim 1, wherein the steering block defines a distal closed end bore and a proximal closed end bore, wherein an end of the first steering cable is anchored to the steering block in the distal closed end bore and an end of the second steering cable is anchored to the steering block in the proximal closed end bore.

3. The device of claim 1, wherein the handle comprises a curved rib, wherein the second steering cable extends along the curved rib.

4. The device of claim 3, wherein the curved rib is C-shaped.

5. The device of claim 1, wherein the handle comprises a base portion and a stem extending distally from the base portion, wherein the knob is rotatably coupled to the base portion and the shaft extends from the stem.

6. The device of claim 5, wherein the stem comprises a neck comprising opposing surfaces spaced apart by a distance to accommodate adjacent fingers from a user, and a head extending radially outwardly from the neck.

7. The device of claim 5, further comprising a mounting block seated within the stem, wherein the proximal portion of the shaft is mounted to the mounting block.

8. The device of claim 1, wherein the knob is rotatable in a plane perpendicular to an axis of the proximal portion of the shaft.

9. A device for creating a cavity or a channel in bone, the device comprising:
    a handle comprising opposing shells defining an interior of the handle, wherein at least one of the opposing shells is formed with a curved rib disposed within the interior of the handle;
    a shaft coupled to the handle and comprising a proximal portion seated within the handle, a tip located forward of the handle, and a flexible elbow between the proximal portion and the tip;
    a first steering cable coupled to the flexible elbow or the tip of the shaft;
    a second steering cable coupled to the flexible elbow or the tip of the shaft; and
    a control assembly operably coupled to the first steering cable and the second steering cable,
    wherein the second steering cable extends along a surface of the curved rib to orient an end of the second steering cable to be coupled to the control assembly to provide for simultaneous tensioning and slackening of the first steering cable and the second steering cable.

10. The device of claim 9, wherein the curved rib is C-shaped.

11. The device of claim 9, wherein the surface faces proximally and downwardly.

12. The device of claim 9, wherein the first steering cable extends along a linear path.

13. The device of claim 9, further comprising a control assembly comprising a steering block axially movable within the handle, wherein an end of the first steering cable and an end of the second steering cable are anchored to the steering block and coaxially arranged.

\* \* \* \* \*